(12) United States Patent
Lee et al.

(10) Patent No.: US 11,471,540 B2
(45) Date of Patent: Oct. 18, 2022

(54) LACTOFERRIN-BASED GENE CARRIER FOR TYPE 2 DIABETES TREATMENT

(71) Applicant: INDUSTRY-UNIVERSITY COOPERATION FOUNDATION HANYANG UNIVERSITY, Seoul (KR)

(72) Inventors: Dong Yun Lee, Seoul (KR); Chang Woo Lee, Seoul (KR); Seungah Lee, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 69 days.

(21) Appl. No.: 16/651,195

(22) PCT Filed: Sep. 21, 2018

(86) PCT No.: PCT/KR2018/011336
§ 371 (c)(1),
(2) Date: Mar. 26, 2020

(87) PCT Pub. No.: WO2019/066442
PCT Pub. Date: Apr. 4, 2019

(65) Prior Publication Data
US 2020/0254114 A1 Aug. 13, 2020

(30) Foreign Application Priority Data
Sep. 27, 2017 (KR) .................. 10-2017-0124935
Sep. 7, 2018 (KR) .................. 10-2018-0107204

(51) Int. Cl.
| | | |
|---|---|---|
| A61K 48/00 | (2006.01) | |
| A61P 3/10 | (2006.01) | |
| A61K 47/61 | (2017.01) | |
| A61K 47/60 | (2017.01) | |

(52) U.S. Cl.
CPC .......... *A61K 48/0075* (2013.01); *A61K 47/60* (2017.08); *A61K 47/61* (2017.08); *A61K 48/0041* (2013.01); *A61P 3/10* (2018.01)

(58) Field of Classification Search
CPC .... A61K 48/0075; A61K 47/60; A61K 47/61; A61K 48/0041; A61K 48/0025; A61K 47/36; A61P 3/10
See application file for complete search history.

(56) References Cited

U.S. PATENT DOCUMENTS

| | | | | |
|---|---|---|---|---|
| 8,124,094 B2 * | 2/2012 | Kim | .................. | A61K 47/6835 424/178.1 |
| 10,487,128 B2 * | 11/2019 | Park | .................... | C07K 14/435 |
| 2011/0009313 A1 | 1/2011 | Sato | | |

FOREIGN PATENT DOCUMENTS

WO 2016/020217 A1 2/2016

OTHER PUBLICATIONS

Huang et al. The use of lactoferrin as a ligand for targeting the polyamidoamine-based gene delivery system to the brain. Biomaterials vol. 29 (2008) pp. 238-246. (Year: 2008).*
Goyal et al. Lactoferrin-conjugated pH and redox-sensitive polymersomes based on PEG-S-S-PLA-PCL-OH boost delivery of bacosides to the brain. Nanoscale, 2018, 10, pp. 17781-17798. (Year: 2018).*
Huang et al. In Vitro and in Vivo Evaluation of Lactoferrin-Conjugated Liposomes as a Novel Carrier to Improve the Brain Delivery. Int. J. Mol. Sci. 2013, 14, pp. 2862-2874. (Year: 2013).*
Hu et al. Lactoferrin-conjugated PEG-PLA nanoparticles with improved brain delivery: In vitro and in vivo evaluations. Journal of Controlled Release 134 (2009) pp. 55-61. (Year: 2009).*
Hu et al. Lactoferrin conjugated PEG-PLGA nanoparticles for brain delivery: Preparation, characterization and efficacy in Parkinson's disease. International Journal of Pharmaceutics. vol. 415, Issues 1-2, Aug. 30, 2011, pp. 273-283. (Year: 2011).*
Hiraku Onishi et al., "Preparation of chitosan/alginate/calcium complex microparticles loaded with lactoferrin and their efficacy on carrageenan-induced edema in rats", Drug Development and Industrial Pharmacy, 2010, pp. 879-884, vol. 36, No. 8.
"*Homo sapiens* fibroblast growth factor 21, mRNA (cDNA clone MGC:21502 IMAGE:3881069), complete cds", NCBI, GenBank accession No. BC018404.1, Jul. 15, 2006, 2 pages.
Akihiko Sugiyama et al., "PEGylated lactoferrin enhanced its hepatoprotective effects on acute liver injury induced by carbon tetrachloride in rats", FOOD and Chemical Toxicology, 2009, pp. 1453-1458, vol. 47, No. 7.
Rongqin Huang et al., "Neuroprotection in a 6-hydroxydopamine-lesioned Parkinson model using lactoferrin-modified nanoparticles", The Journal of Gene Medicine, 2009, pp. 754-763, vol. 11.
Yi-Rac Choi et al., Polymer Science and Technology, Aug. 4, 2004, pp. 402-410, vol. 15. No. 4.
Xudong Yao et al., "Oral Delivery of Lactoferrin: A Review", International Journal of Peptide Research and Therapeutics, 2013, pp. 125-134, 19.
Notification of Reason for Refusal for corresponding KR 10-2018-0107204, dated Nov. 21, 2019.
International Search Report for PCT/KR2018/011336, dated May 29, 2019.

* cited by examiner

*Primary Examiner* — Marcela M Cordero Garcia
(74) *Attorney, Agent, or Firm* — Sughrue Mion, PLLC

(57) ABSTRACT

The present invention relates to a gene delivery complex comprising: a biocompatible polymer backbone; and pegylated lactoferrin connected to the biocompatible polymer backbone by means of a covalent bond. The gene delivery complex is orally administered into an individual, can be absorbed in vivo by means of a lactoferrin receptor, and enables the in vivo delivery of a target gene and the expression thereof.

10 Claims, 25 Drawing Sheets
Specification includes a Sequence Listing.

SEQUENCE LISTING

<160> NUMBER OF SEQ ID NOS: 1

<210> SEQ ID NO 1
<211> LENGTH: 1362
<212> TYPE: DNA
<213> ORGANISM: Homo sapiens

<400> SEQUENCE: 1

```
gaggcttcca aggcaggata cttgtgtctc agatgcggtc gcttctttca tacagcaatt      60
gccgccttgc tgaggatcaa ggaacctcag tgtcagatca cgccctcccc ccaaacttag     120
aaattcagat ggggcgcaga aatttctctt gttctgcgtg atctgcatag atggtccaag     180
aggtggtttt tccaggagcc cagcacccct cctccctccg actcagaccc aggagtctgg     240
ccctccattg aaaggacccc aggttacatc atccattcag gctgcccttg ccacgatgga     300
attctgtagc tcctgccaaa tgggtcaaat atcatggttc aggcgcaggg agggtgattg     360
ggcgggcctg tctgggtata aattctggag cttctgcatc tatcccaaaa aacaagggtg     420
ttctgtcagc tgaggatcca gccgaaagag gagccaggca ctcaggccac ctgagtctac     480
tcacctggac aactggaatc tggcaccaat tctaaaccac tcagcttctc cgagctcaca     540
ccccggagat cacctgagga cccgagccat tgatggactc ggacgagacc gggttcgagc     600
actcagggct gtgggtttct gtgctggctg gtcttctgct gggagcctgc caggcacacc     660
ccatccctga ctccagtcct ctcctgcaat tcgggggcca agtccggcag cggtacctct     720
acacagatga tgcccagcag acagaagccc acctggagat cagggaggat gggacggtgg     780
ggggcgctgc tgaccagagc cccgaaagtc tcctgcagct gaaagccttg aagccgggag     840
ttattcaaat cttgggagtc aagacatcca ggttcctgtg ccagcggcca gatgggggcccc   900 tgtatggatc gctccacttt gaccctgagg cctgcagctt ccgggagctg cttcttgagg     960
acggatacaa tgtttaccag tccgaagccc acggcctccc gctgcacctg ccagggaaca    1020
agtccccaca ccgggaccct gcaccccgag gaccagctcg cttcctgcca ctaccaggcc    1080 tgcccccgc accccggag ccaccggaa tcctggcccc cagccccc gatgtgggct    1140 cctcggaccc tctgagcatg gtgggacctt cccagggccg aagcccagc tacgcttcct    1200 gaagccagag gctgtttact atgacatctc ctctttattt attaggttat ttatcttatt    1260
tattttttta tttttcttac ttgagataat aaagagttct agaggaggat aaaaaaaaaa    1320
aaaaaaaaaa aaaaaaaaaa aaaaaaaaaa aaaaaaaaaa aa                      1362
```

LACTOFERRIN-BASED GENE CARRIER FOR TYPE 2 DIABETES TREATMENT

CROSS REFERENCE TO RELATED APPLICATIONS

This application is a National Stage of International Application No. PCT/KR2018/011336, filed Sep. 21, 2018, claiming priority based on Korean Patent Application No. 10-2017-124935 filed Sep. 27, 2017 and Korean Patent Application No. 10-2018-0107204 filed Sep. 7, 2018.

TECHNICAL FIELD

The present invention relates to a lactoferrin-based orally administered gene carrier for the treatment of type 2 diabetes mellitus.

BACKGROUND ART 8.3% of adults suffer from diabetes worldwide, and the number of patients with diabetes is annually increasing by about 4 to 6%. Diabetes mellitus may be classified into type 1 diabetes mellitus which occurs because insulin is not secreted from beta cells (β cells) of the pancreas and type 2 diabetes mellitus that occurs because insulin resistance is increased despite the secretion of insulin. In type 2 diabetes mellitus, insulin resistance is caused by sustained hyperglycemia for a long period of time, and when insulin resistance is increased, proliferation of beta cells is increased, so that more insulin is produced and overload occurs. As a result, insulin secretion from beta cells becomes insufficient, and hyperglycemia occurs, which causes various complications such as diabetic retinopathy, dyslipidemia, cardiovascular disease, and the like.

As a method for treating type 2 diabetes mellitus, an oral drug administration method of promoting the secretion of insulin by stimulating the pancreas or suppressing the intake and de novo synthesis of glucose and an insulin injection method of directly administering insulin have been used. However, these methods are limited in exhibiting a sustained effect and have various side effects such as vomiting or diarrhea.

Meanwhile, fibroblast growth factor 21 (FGF21) is a protein mainly expressed in the liver and pancreas and acts as a hormone in the circulatory system and is known as a potent regulator of blood glucose level, lipid metabolism and energy homeostasis. Further, FG21 is known to alleviate symptoms of type 2 diabetes mellitus by lowering insulin resistance, decreasing the concentrations of glucose and triglycerides in blood, and reaching various tissues through the blood. However, since FGF21 has a half-life of about 2 hours in the body, there is a limitation that a long-term therapeutic effect cannot be exhibited against type 2 diabetes mellitus. In order to overcome the limitation, the short half-life is overcome by conjugating FGF21 with a polypeptide labeled with polystyrene, but complex processes in polypeptide library construction and purification such as gene screening are required.

Meanwhile, a method of administering LY2405319 which is an analog of FGF21 has also been used, but fails to exhibit significant effects on body weight loss and homeostasis of glucose. In addition, since the analog has the same half-life in the body as FGF21, there is a disadvantage in that a sustained effect cannot be exhibited.

Therefore, in order to alleviate type 2 diabetes mellitus, there is a need for a method capable of increasing the half-life in the body while maintaining the effect of FGF21.

DISCLOSURE

Technical Problem

An object of the present invention is to provide a gene delivery complex comprising: (a) a biocompatible polymer and (b) pegylated lactoferrin connected to the biocompatible polymer by means of a covalent bond.

Another object of the present invention is to provide a gene carrier comprising: a vector comprising a target gene fragment to be delivered in vivo; and a gene delivery complex.

Still another object of the present invention is to provide a pharmaceutical composition for the prevention or treatment of type 2 diabetes mellitus, comprising the gene carrier as an active ingredient.

Technical Solution

To achieve the objects, an aspect of the present invention provides a gene delivery complex comprising (a) a biocompatible polymer and (b) pegylated lactoferrin connected to the biocompatible polymer by means of a covalent bond.

As used herein, the term 'biocompatible polymer' refer to a material that does not induce an adverse response such as an inflammatory response and/or an immune response when introduced in vivo, includes biodegradable and biostable materials, and serves as a backbone capable of binding to a plurality of pegylated lactoferrins.

In an exemplary embodiment of the present invention, the biocompatible polymer may be selected from the group consisting of glycol chitosan, poly lactic acid, poly(lactic-co-glycolic acid), alginate, hyaluronic acid, poly-L-lysine, gelatin, and collagen. Most preferably, the biocompatible polymer may be glycol chitosan, and since glycol chitosan is water-soluble, glycol chitosan is well dissolved in water, and thus can easily move to the esophagus, stomach, and intestines in the body, and has a positive charge, and thus can form an ionic bond with a negatively charged gene. Further, glycol chitosan is known for its ability to be adsorbed onto the serous membranes in the body, and has an advantage in that it is possible to increase the likelihood of absorption during oral absorption.

As used herein, the term 'lactoferrin' refers to a protein present in breast milk, saliva, tears, and the like, is most abundant in colostrum, and shows an activity such as an antibacterial effect, increased immunity, and an anti-inflammatory action. In addition, lactoferrin is ligand that can bind to a low-density lipoprotein receptor related protein (LRP) receptor, which is one of the cell membrane proteins, and the LRP receptor (lactoferrin receptor) is known to be highly expressed in small intestinal epithelium, cerebrovascular endothelial cells, and the like.

In an exemplary embodiment, the pegylated lactoferrin means that lactoferrin is linked to a polyethylene glycol (PEG) polymer, and may be synthesized by heterobifunctional PEG.

The heterobifunctional PEG refers to a PEG in which both ends of the PEG are each substituted with different appropriate functional groups. For example, one end may include a maleimide substituent, and the other end may include a NHS ester substituent. The maleimide substituent is a substituent capable of forming a chemical bond by reacting with a sulfhydryl (—SH) group, and the NHS ester substituent is a substituent capable of forming a chemical bond by reacting with an amine group.

In an exemplary embodiment of the present invention, pegylated lactoferrin may be synthesized by the NHS ester substituent primarily reacting with an amine group of a biocompatible polymer and reacting with lactoferrin having a sulfhydryl (—SH) substituent. In this case, an amine group of lactoferrin may be substituted with a sulfhydryl group using a Traut's reagent.

In an exemplary embodiment of the present invention, a complex of the biocompatible polymer and pegylated lactoferrin connected to the biocompatible polymer by means of a covalent bond is absorbed in vivo by a lactoferrin receptor, and thus may be used for transferring a target gene into the body.

Another aspect of the present invention provides a gene carrier comprising: a vector comprising a target gene fragment to be delivered in vivo; and the above-mentioned gene delivery complex.

In an exemplary embodiment of the present invention, the target gene refers to a gene to be introduced in vivo and expressed, and may be used without limitation as long as the target gene is a gene required for the prevention, alleviation, or treatment of a disease.

In an exemplary embodiment of the present invention, the target gene may be a gene encoding fibroblast growth factor 21 (FGF21), and the target gene fragment may include a polynucleotide sequence represented by SEQ ID No. 1.

In an exemplary embodiment of the present invention, the vector may further include an additional sequence required for the expression of a target gene fragment, and may include, for example, a promoter sequence required for the expression of a gene.

In an exemplary embodiment of the present invention, the gene carrier may include a vector and a gene delivery complex at a binding ratio of 1:2 to 1:15.

Still another aspect of the present invention provides a pharmaceutical composition for the prevention or treatment of type 2 diabetes mellitus, comprising the gene carrier as an active ingredient.

As used herein, the term 'type 2 diabetes mellitus' is also called insulin-independent diabetes, and refers to a state in which little or no insulin is secreted by the pancreas, or the insulin does not work normally even though the insulin is secreted, and the blood glucose level in the body is continuously maintained at a high level.

In an exemplary embodiment of the present invention, the gene carrier may comprise a polynucleotide sequence represented by SEQ ID No. 1.

The pharmaceutical composition of the present invention may comprise a pharmaceutically acceptable carrier in addition to the active ingredient. In this case, the pharmaceutically acceptable carrier is typically used during formulation, and includes lactose, dextrose, sucrose, sorbitol, mannitol, starch, acacia rubber, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, and is not limited thereto. Furthermore, the pharmaceutically acceptable carrier may further comprise a lubricant, a wetting agent, a sweetening agent, a flavoring agent, an emulsifying agent, a suspending agent, a preservative, and the like in addition to the ingredients.

The pharmaceutical composition of the present invention may be administered orally or parenterally (for example, intravenous, subcutaneous, intraperitoneal or applied topically) according to the target method. However, the composition of the present invention may be orally administered because the composition is easily absorbed by interaction with a LRP receptor expressed in small intestinal endothelial cells. When the active ingredient of the present invention is formulated into a preparation such as tablets, capsules, chewable tablets, a powder, a liquid, and a suspension for the purpose of oral administration, it is possible to comprise a binder such as arabic rubber, corn starch, microcrystalline cellulose or gelatin, an excipient such as calcium diphosphate or lactose, a disintegrant such as alginic acid, corn starch, or potato starch, a lubricant such as magnesium stearate, a sweetening agent such as sucrose or saccharin, and a flavoring agent such as peppermint, methyl salicylate, or fruit flavor.

The pharmaceutical composition of the present invention is administered in a pharmaceutically effective amount. In the present invention, the 'pharmaceutically effective amount' refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by the person skilled in the art.

Advantageous Effects

A gene carrier complex disclosed in the present invention comprising a biocompatible polymer backbone and pegylated lactoferrin connected to the biocompatible polymer backbone by means of a covalent bond can be orally administered into an individual to be absorbed in vivo by means of a lactoferrin receptor, so that a target gene can be delivered in vivo and expressed.

MODES OF THE INVENTION

Hereinafter, one or more specific exemplary embodiments will be described in more detail through Examples. However, these Examples are provided only for exemplarily explaining the one or more specific exemplary embodiments, and the scope of the present invention is not limited to these Examples.

Example 1: Synthesis of Glycol Chitosan-PEG-Lactoferrin 1-1. Synthesis of Glycol Chitosan-PEG-Lactoferrin After glycol chitosan (hereinafter, referred to as gCS) was dissolved in phosphate buffered saline (PBS; pH 8.0), N-hydroxylsuccinimide polyethylene glycol maleimide (NHS-PEG-MAL) was added thereto and the resulting mixture was reacted for 20 minutes. A reactant (gCS-PEG-hydrolyzed MAL) in the form of a powder was obtained by dialyzing the reaction solution for 12 hours or more and freeze-drying the dialysate.

Ethylenediaminetetraacetic acid sodium salt (sodium EDTA) was dissolved in PBS (pH 8.0), and lactoferrin (hereinafter, referred to as Lf) and a Traut's solution were put into the resulting solution, and the resulting mixture was reacted for 1 hour. After the reaction, dialysis was performed in a refrigerator for 12 hours or more. The reactant powder (gCS-PEG-hydrolyzed MAL) was dissolved in PBS (pH 6.8), the dialyzed lactoferrin reactant (including SH-Lf) was added thereto, and the resulting mixture was reacted for 1 hour. Thereafter, dialysis was performed for 12 hours or more, the dialysate was freeze-dried, and then gCS-PEG-Lf in the form of a powder was obtained.

Figure 1A:
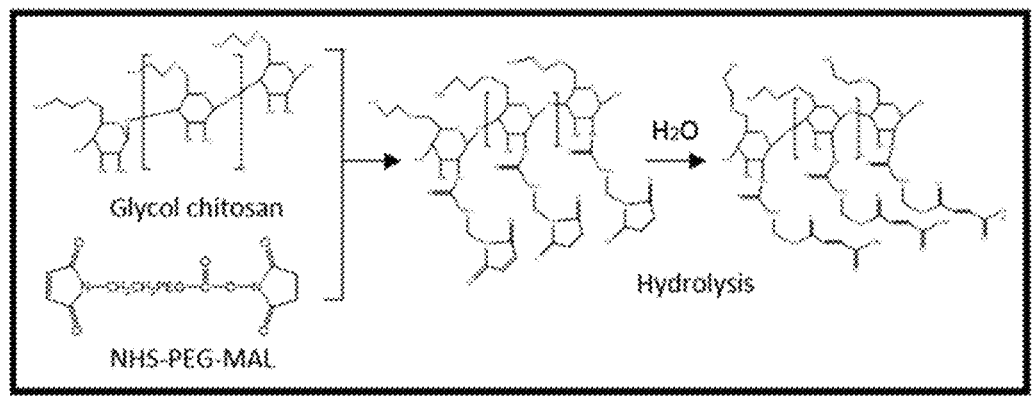
FIG. 1A illustrates a process of synthesizing gCS-PEG-hydrolyzed MAL by reacting glycol chitosan (gCS) with N-hydroxylsuccinimide polyethylene glycol maleimide (NHS-PEG-MAL)
Figure 1B:
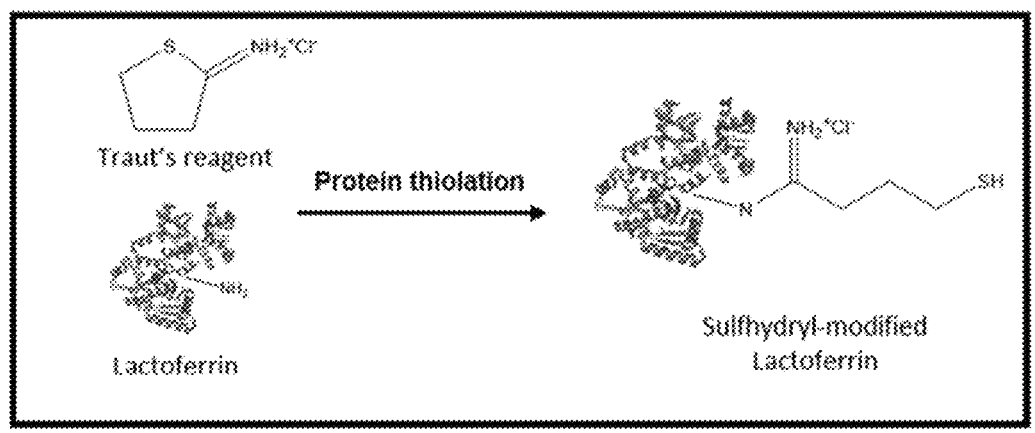
FIG. 1B illustrates a process of synthesizing thiolated LF (SH-Lf) by reacting a Traut's solution with lactoferrin (Lf)
Figure 1C:
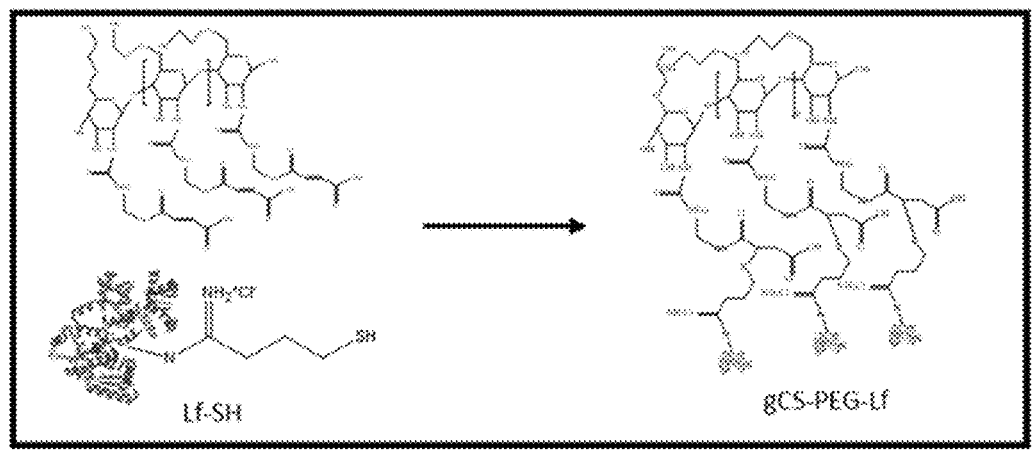
FIG. 1C illustrates a process of synthesizing gCS-PEG-Lf by reacting gCS-PEG-hydrolyzed MAL with SH-Lf.

FIG. 1 schematically illustrates the glycol chitosan-PEG-lactoferrin synthesis process.

1-2. Confirmation of Synthesized gCS-PEG-Lf

The materials before the synthesis, gCS and NHS-PEG-MAL, and the synthesized materials gCS-PEG-hydrolyzed MAL and gCS-PEG-Lf were analyzed by attenuated total reflectance-Fourier transform infrared spectroscopy (ATR-FTIR).

Figure 2A:
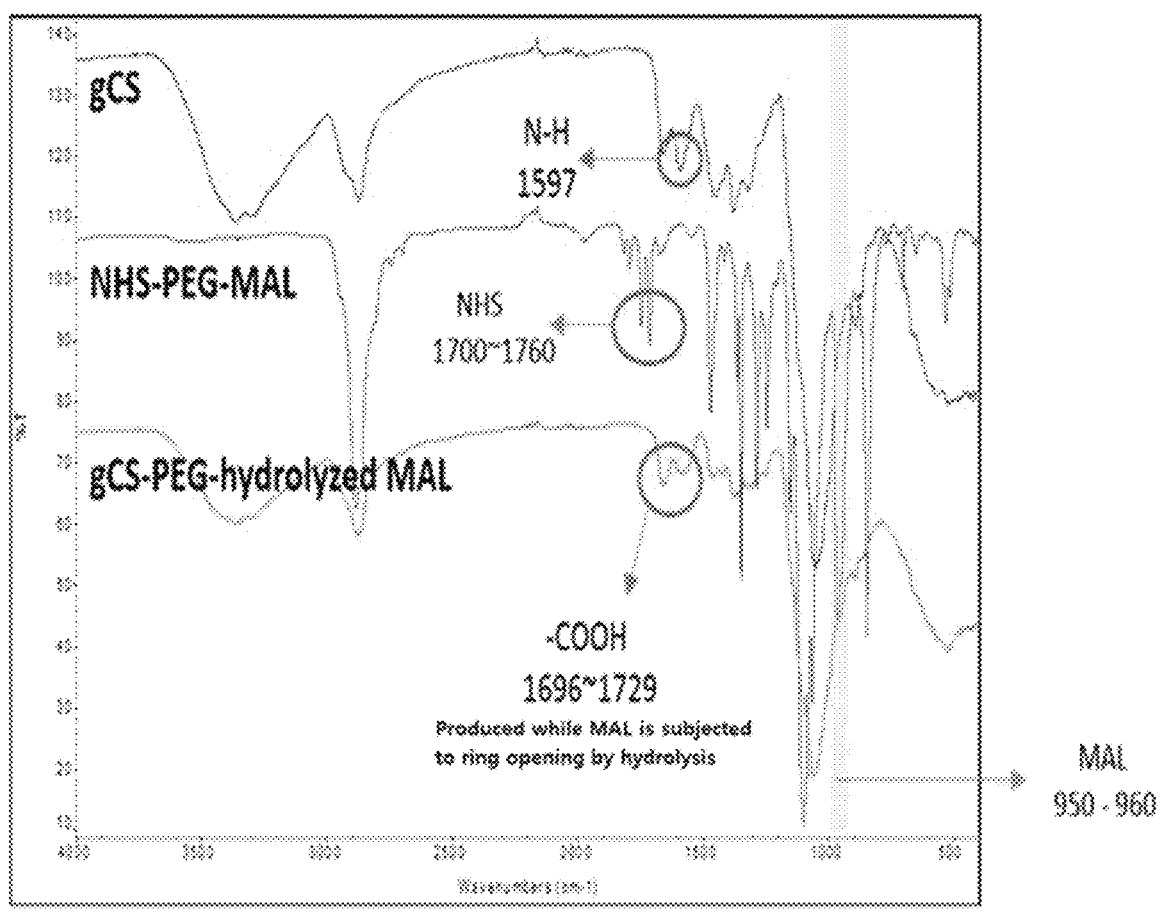
FIG. 2A illustrates the attenuated total reflectance-Fourier transform infrared spectroscopy (ATR-FTIR) analysis results of gCS, NHS-PEG-MAL, and gCS-PEG-hydrolyzed MAL.

As a result, as illustrated in FIG. 2A, it could be confirmed that in the synthesized material gCS-PEG-hydrolyzed MAL, peaks at 3382 cm$^{-1}$ and 3300 cm$^{-1}$ corresponding to gCS and peaks at 2875 cm$^{-1}$ and 520 cm$^{-1}$ corresponding to NHS-PEG-MAL were all present. The peak corresponding to COOH newly formed by a hydrolysis reaction of MAL could be confirmed at 1696 to 1729 cm$^{-1}$.

Figure 2B:
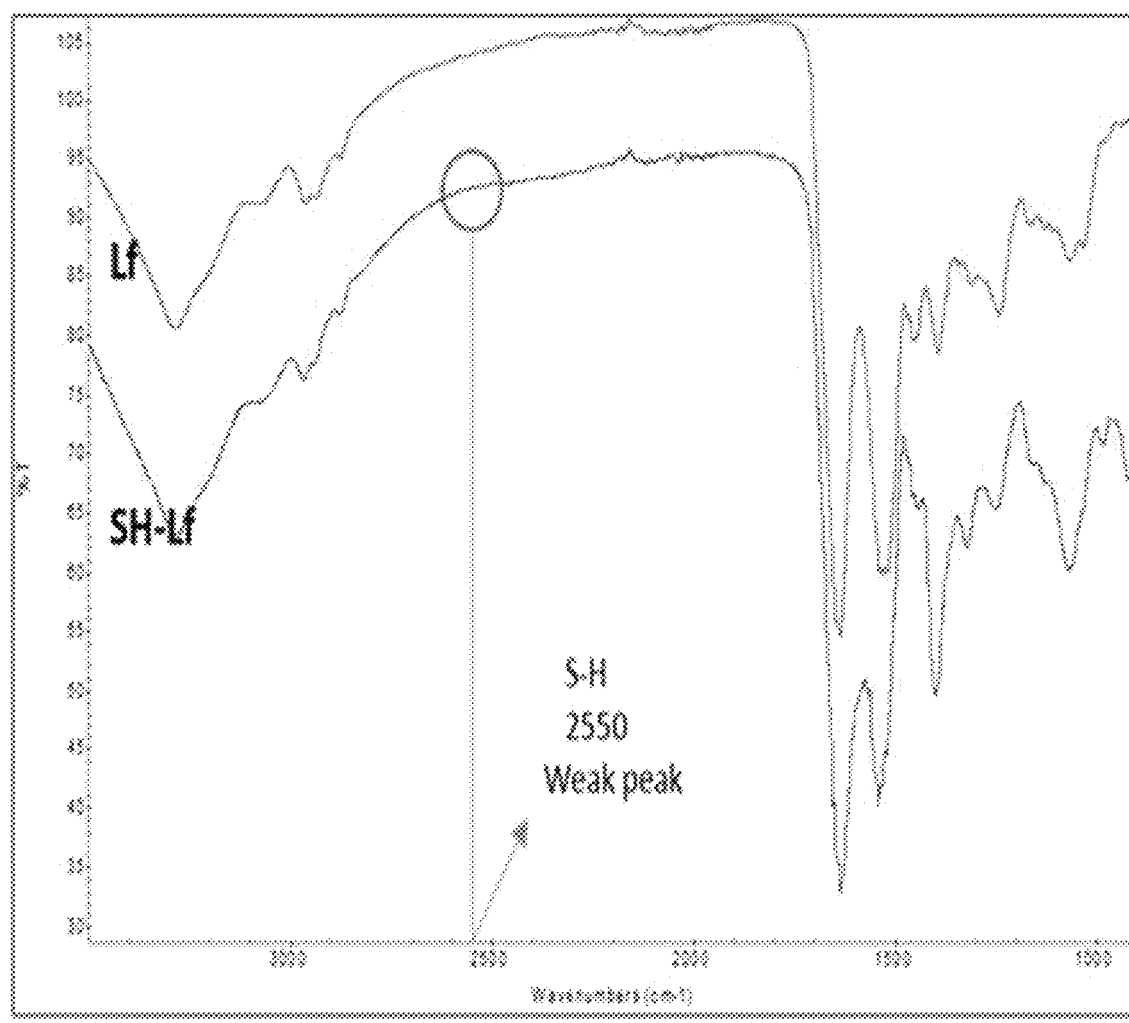
FIG. 2B illustrates the ATR-FTIR analysis results of Lf and SH-Lf.

Further, as illustrated in FIG. 2B, it could be seen that in the thiolated Lf (SH-Lf), peaks (1630 cm$^{-1}$, 1525 cm$^{-1}$) corresponding to existing Lf were present, and a new peak (2550 cm$^{-1}$) for S—H was formed.

Figure 2C:
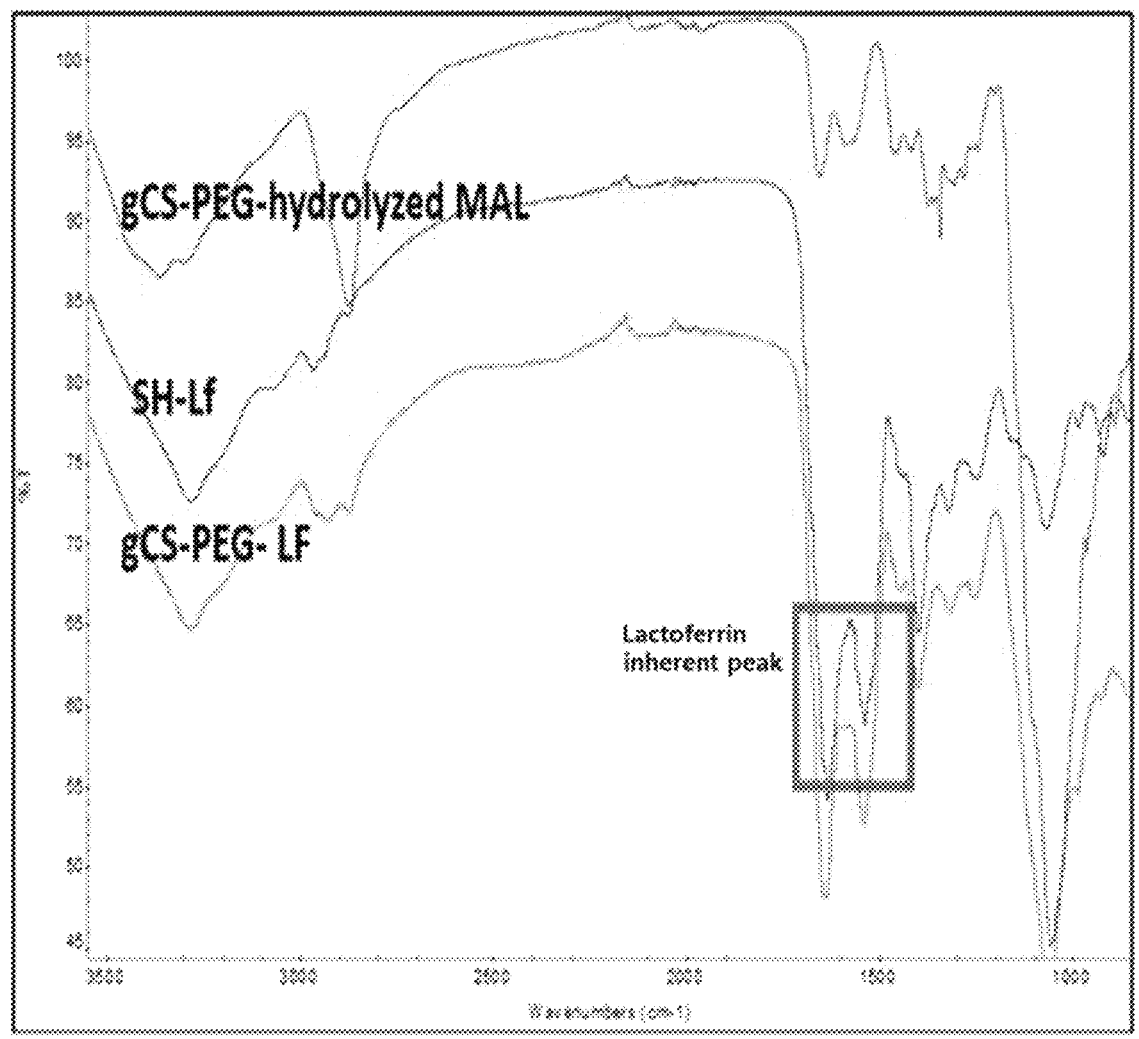
FIG. 2C illustrates the ATR-FTIR analysis results of gCS-PEG-hydrolyzed MAL, SH-Lf, and gCS-PEG-Lf.

In addition, as illustrated in FIG. 2C, as a result of analyzing gCS-PEG-Lf, it could be seen that peaks (1630 cm$^{-1}$, 1525 cm$^{-1}$) corresponding to existing Lf were present, and gCS-PEG-Lf had a peak (1050 cm$^{-1}$) corresponding to gCS-PEG-MAL.

Example 2: Confirmation of Cytotoxicity of gCS-PEG-Lf

Figure 3A:
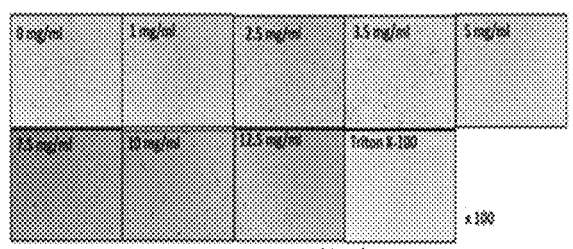
FIG. 3A illustrates the results of observing cells by an optical microscope after treating Caco-2 cells with gCS-PEG-Lf, and FIGS. 3B and C illustrate the results of confirming the presence or absence of cytotoxicity with a Live and Dead Cell Kit and a cell counting kit-8 (CCK-8) after treating Caco-2 cells with gCS-PEG-Lf.

As a result of treating small intestine epithelium-derived cells Caco-2 cells with gCS-PEG-Lf at different concentrations (0, 1, 2.5, 3.5, 5, 7.5, 10, and 12.5 mg/ml), as illustrated in FIG. 3A, it could be confirmed by an optical microscope that as the concentration of gCS-PEG-Lf treatment was increased, Caco-2 cells were killed.

Figure 3B:
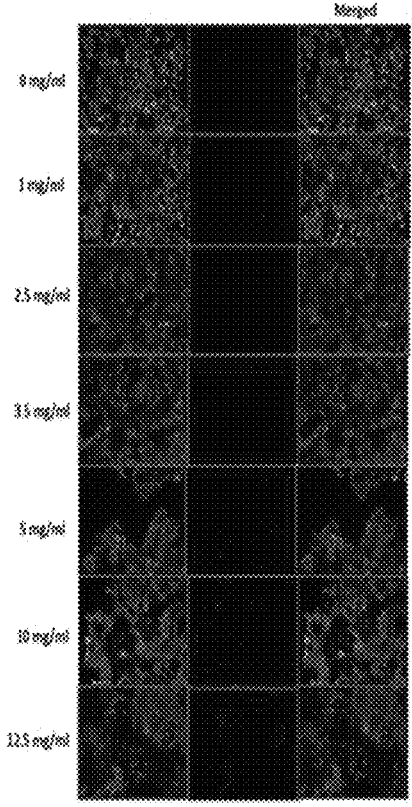

Furthermore, the same experiment was performed using a Live and Dead Cell Kit (Sigma-Aldrich, USA). As a result, as illustrated in FIG. 3B, it could be seen that as the concentration of gCS-PEG-Lf was increased, red fluorescence was increased, indicating that the death of Caco-2 cells was increased.

Figure 3C:
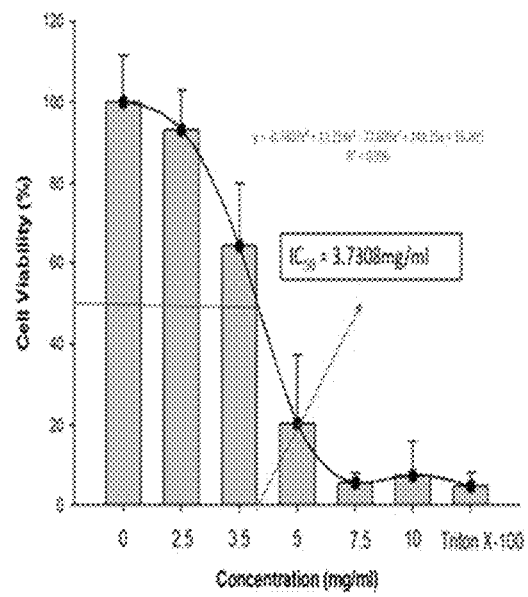

After Caco-2 cells were treated with gCS-PEG-Lf for 24 hours, cell viability was confirmed by a cell counting kit-8 (CCK-8). As a result, as illustrated in FIG. 3C, it could be quantitatively seen that as the concentration of gCS-PEG-Lf was increased, the viability of Caco-2 cells was decreased. Further, it was confirmed that the IC$_{50}$ value of gCS-PEG-Lf was 3.7308 mg/ml.

Example 3: Confirmation of Endocytosis of gCS-PEG-Lf by Lactoferrin Receptor A monolayer was formed by culturing Caco-2 cells in a transwell plate with a pore size of 0.4 μm, and a transepithelial electrical resistance (TEER) experiment was performed.

Cultured Caco-2 cells (2×10$^4$ cells/insert) were divided into a control (Con), a gCS (1,000 μg/ml) treatment group, a gCS-PEG treatment group, a gCS-PEG-Lf (1,000 μg/ml) treatment group, and a Lf+gCS-PEG-Lf treatment group and TEER values over time were measured after the corresponding treatment was performed. The Lf+gCS-PEG-Lf treatment group was treated with gCS-PEG-Lf (1,000 μg/ml) after an Lf receptor was saturated with Lf (1,000 μg/ml) for 3 hours.

Figure 4:
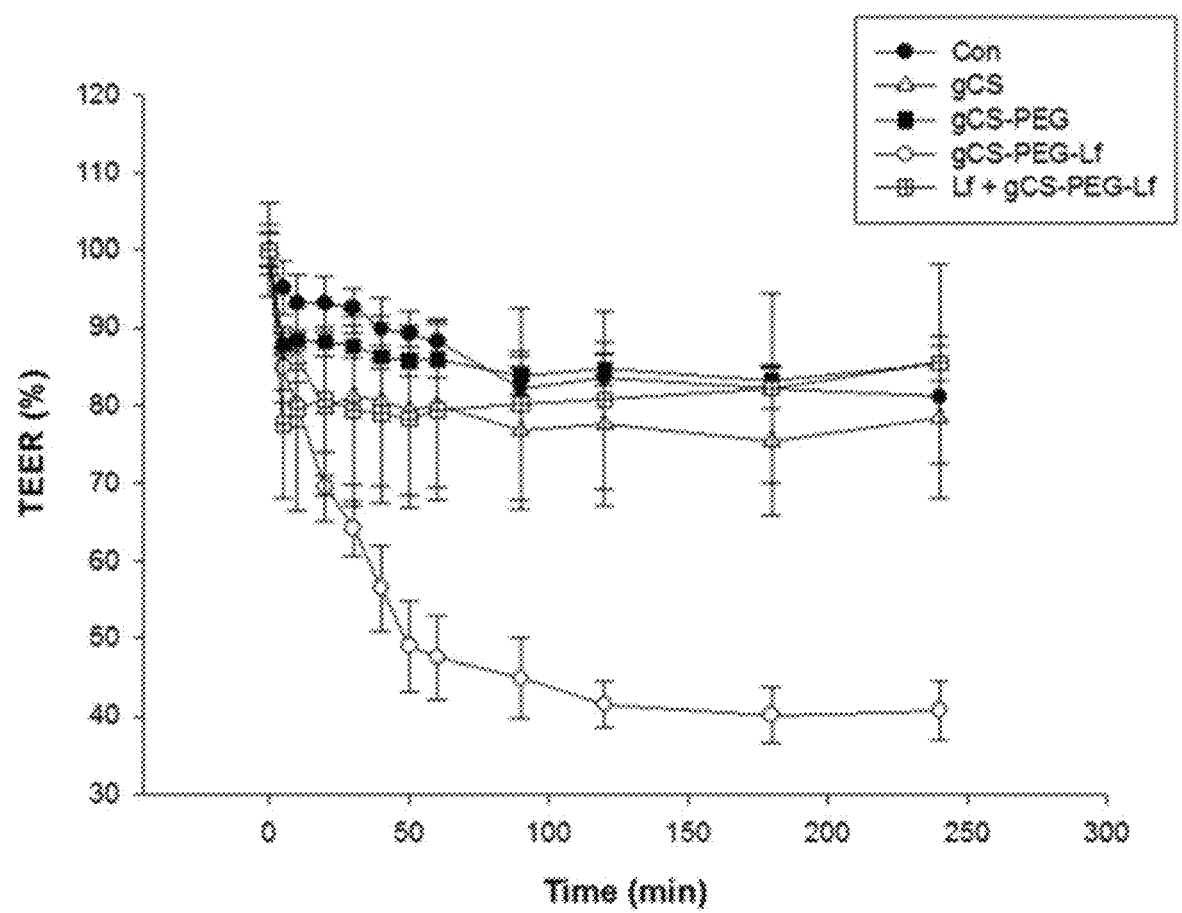
FIG. 4 illustrates the results of confirming the presence or absence of endocytosis of gCS-PEG-Lf by a lactoferrin receptor through a transepithelial electrical resistance (TEER) experiment.

As a result of measurement, as illustrated in FIG. 4, it could be confirmed that, compared to the treatment group with unbound Lf, the TEER value was reduced over time in the gCS-PEG-Lf treatment group. However, it could be seen that gCS-PEG-Lf was endocytosed by the Lf receptor by confirming that the TEER value was not decreased in the Lf+gCS-PEG-Lf treatment group.

Example 4: Confirmation of Binding Ratio of gCS-PEG-Lf and DNA 4-1. Gel Retardation Experiment A reaction was carried out for 30 minutes by varying the binding ratio of 5 μg of the GFP gene and gCS-PEG-Lf (0, 5, 10, 15, 20, 35, and 50 μg). After the completion of the reaction, the product was loaded onto an agarose gel and electrophoresed at 100 V for 40 minutes.

Figure 5:
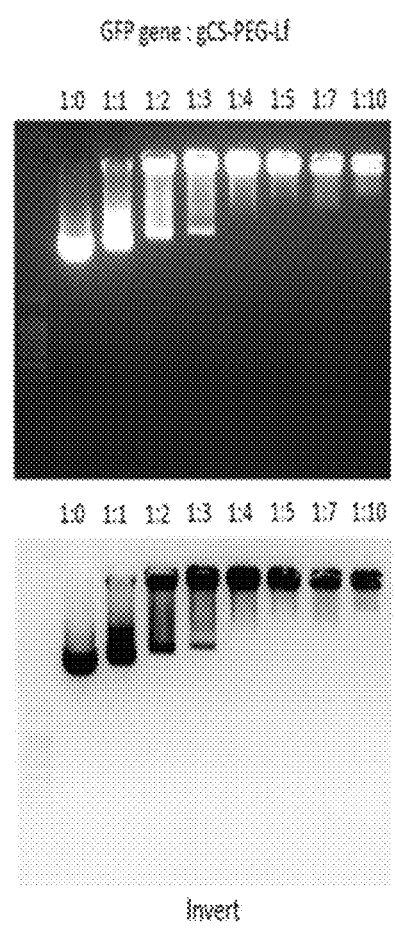
FIG. 5 illustrates the results of performing a gel retardation experiment after reacting a GFP gene with gCS-PEG-Lf by modifying the binding ratio of the GFP gene to the gCS-PEG-Lf.

As a result, as illustrated in FIG. 5, it could be confirmed that as the ratio of the GFP gene and the gCS-PEG-Lf was increased, the binding force of the GFP gene and the gCS-PEG-Lf was increased. Furthermore, it could be seen that when the binding ratio (mass ratio) of the GFP gene and the gCS-PEG-Lf was 4 or higher, the GFP gene was bound to the gCS-PEG-Lf in the most ideal manner.

4-2. Measurement of Zeta Size and Zeta Potential

After carrying out a reaction for 30 minutes by varying the binding ratio of the GFP gene and the gCS-PEG-Lf, a 0.2 mg/ml reaction solution was put into a disposable cuvette and mixed well. The Zeta potential and Zeta size of the GFP/gCS-PEG-Lf solution were measured using a dynamic light scattering (DLS) device.

Figure 6A:
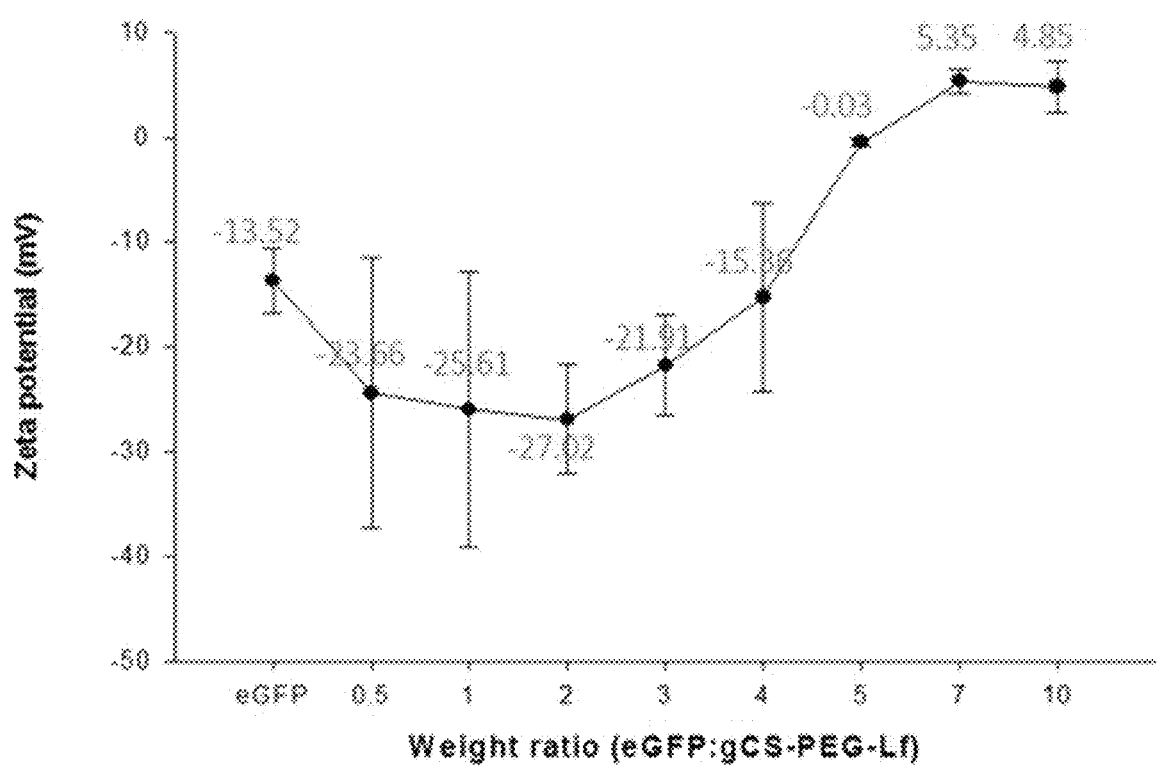
FIG. 6A illustrates the results of measuring the Zeta potential of a reaction solution after reacting a GFP gene with gCS-PEG-Lf by modifying the binding ratio of the GFP gene to the gCS-PEG-Lf.
Figure 6B:
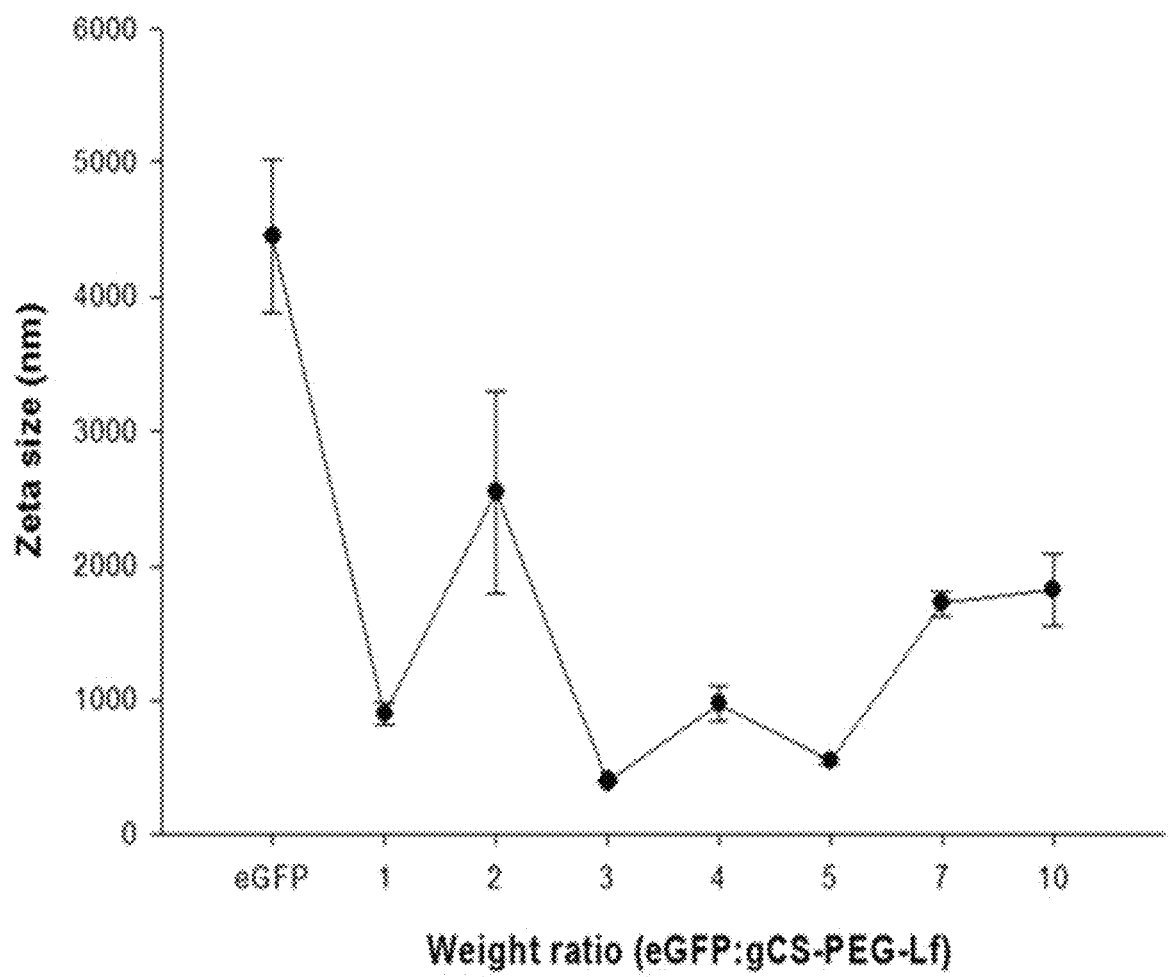
FIG. 6B illustrates the results of measuring the Zeta size of a reaction solution after reacting a GFP gene with gCS-PEG-Lf by modifying the binding ratio of the GFP gene to the gCS-PEG-Lf.

As a result, as illustrated in the Zeta potential graph shown in FIG. 6A, it could be seen that a negative charge appeared due to a phosphoric acid group present in the GFP gene, a positive charge appeared due to gCS-PEG-Lf, and when the binding ratio of the GFP gene and the gCS-PEG-Lf was 1:5, a charge closest to 0 appeared. In addition, in the Zeta size graph shown in FIG. 6B, it was confirmed that when the binding ratio of the GFP gene and the gCS-PEG-Lf was 1:3 or 1:5, the smallest size was exhibited.

Example 5: Confirmation of Targeting of gCS-PEG-Lf by Oral Administration

The gCS-PEG-Lf synthesized to treat type 2 diabetes mellitus is absorbed in vivo and delivered to tissues after oral administration. Since the gCS-PEG-Lf encounters an acidic pH environment, proteolytic enzymes, and the like in the stomach during the process of reaching each tissue, it was confirmed whether the gCS-PEG-Lf was stably delivered to tissues under such an environment.

The GFP/gCS-PEG-Lf was orally administered at a concentration of 100 μg/500 μg per mouse, and the brain, the heart, the duodenum, the jejunum, the ileum, the kidneys, the liver, the pancreas, the spleen, and the lungs were isolated by sacrificing the mouse three days later. A tissue block was prepared by embedding the isolated tissues in an OCT compound, and the tissue block was frozen in a cryogenic refrigerator for 24 hours. Thereafter, the tissue block was subjected to cryosection, hematoxylin & eosin staining, and observed under an optical microscope. Further, the degree of GFP expression was confirmed by an optical microscope.

Figure 7:
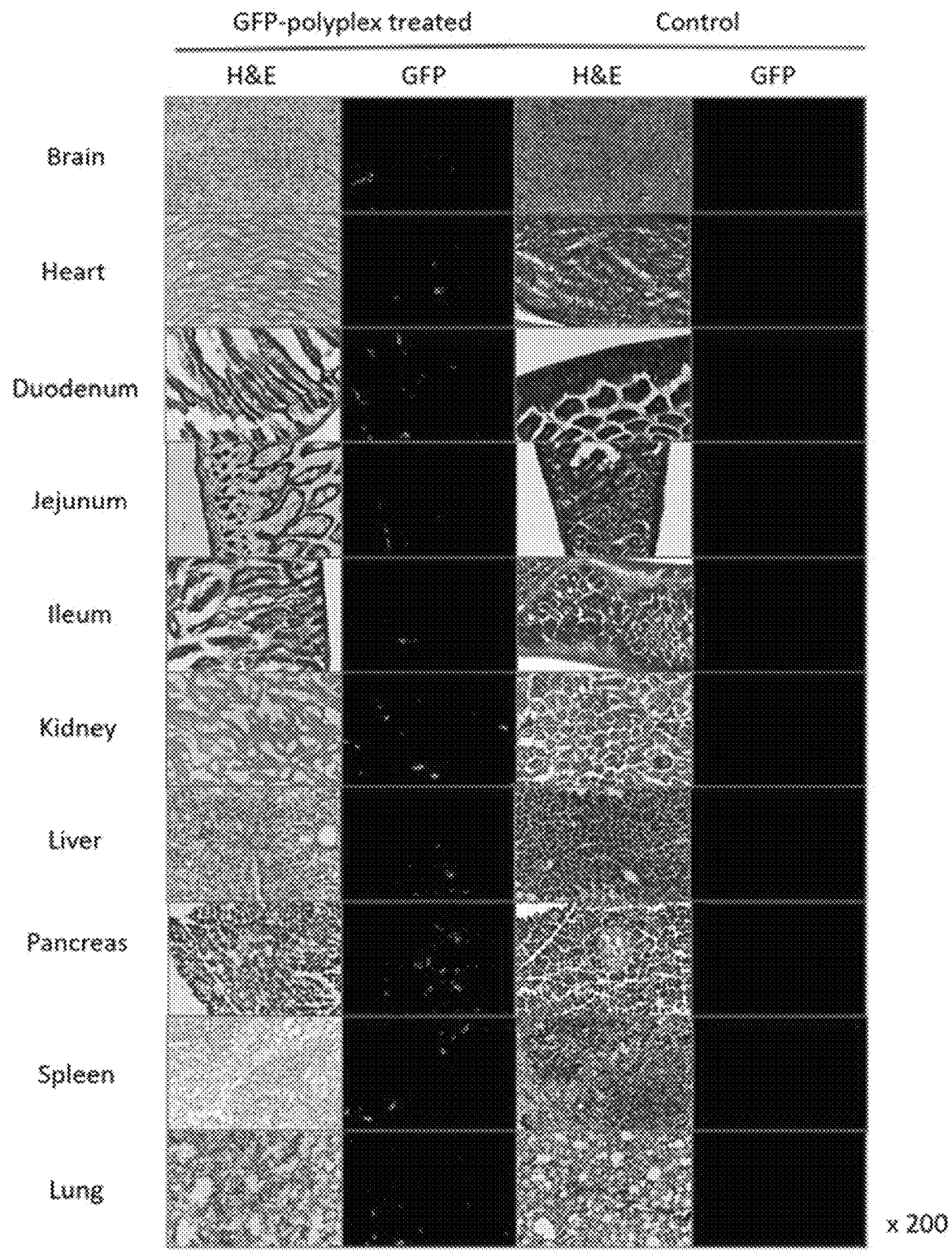
FIG. 7 illustrates the results of isolating each tissue and staining the tissue with hematoxylin & eosin after orally administering GFP/gCS-PEG-Lf to mice and the results of confirming the expression levels of GFP.

As a result, as illustrated in FIG. 7, GFP fluorescence signals could be confirmed in each tissue when the GFP/gCS-PEG-Lf was orally administered, as compared to the control. This means that the GFP/gCS-PEG-Lf is stably delivered to each tissue.

Figure 8:
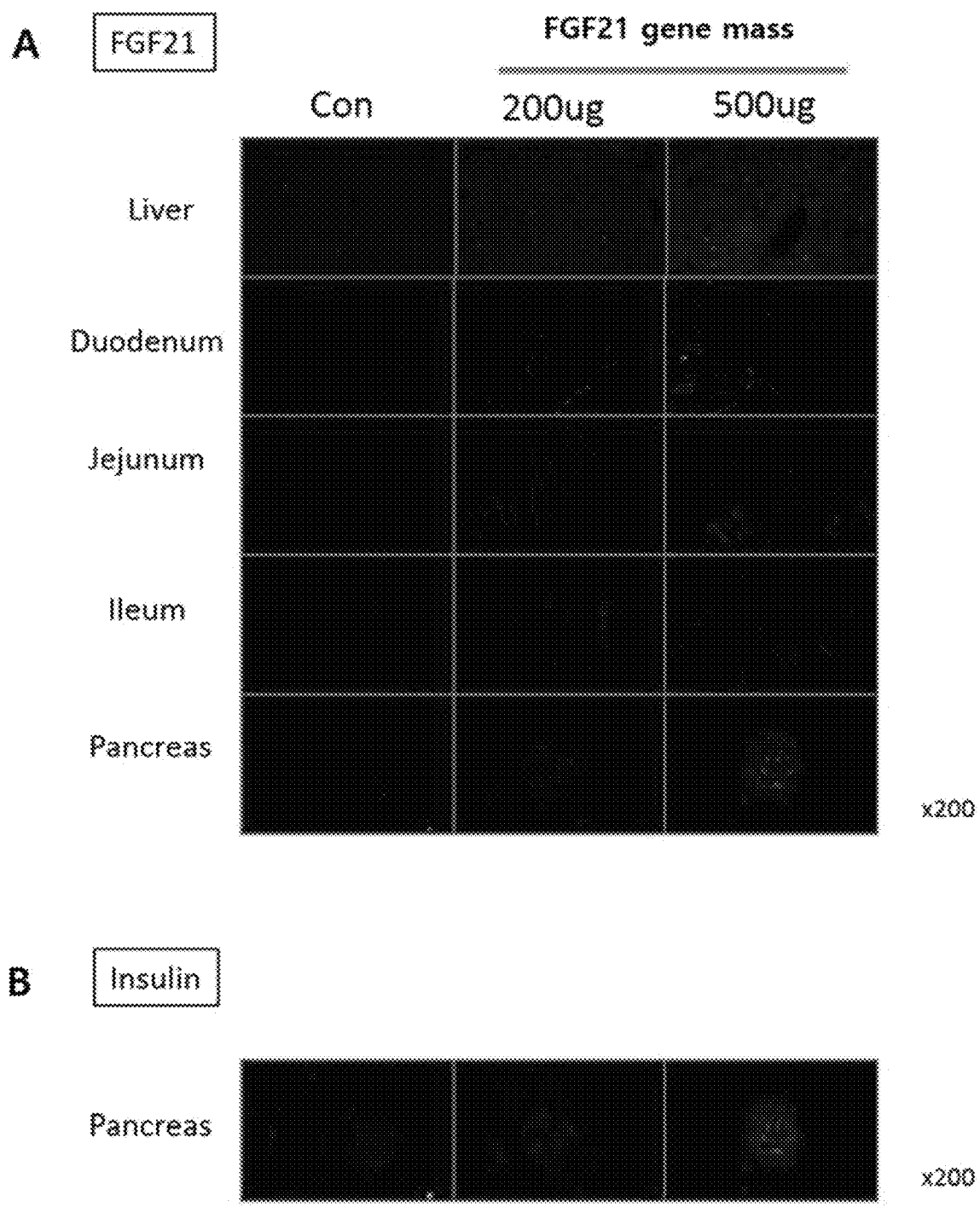
FIG. 8 illustrates the results of confirming the expression levels of fibroblast growth factor 21 (FGF21) and insulin by isolating each tissue after orally administering FGF21/gCS-PEG-Lf to mice.

Example 6: Comparison of Expression Levels of FGF21 and Insulin According to Dosage of FGF21 Gene The FGF21 gene of SEQ ID No. 1 was used by being inserted into the EcoRI and SalI sites of a pCMV6-XL5 plasmid vector (ORIGENE, 4.7 kb). FGF21/gCS-PEG-Lf (FGF21 gene:gCS-PEG-Lf=1:5) including the FGF21 gene (200 or 500 μg) was orally administered to a mouse, and the liver, the duodenum, the jejunum, the ileum, and the pancreas were isolated by sacrificing the mouse three days later. The isolated organs were fixed with paraffin and then cut to prepare a tissue section, which was then subjected to immunohistochemistry (IHC) staining with an FGF21 antibody and an insulin antibody. As a result, as illustrated in FIG. 8, it could be confirmed that the higher the oral dose of the FGF21 gene was, the higher the expression levels of the FGF21 protein and insulin were. Based on this result, the oral dose of the FGF21 gene to be used in in vivo experiments was determined.

Example 7: Comparison of Blood FGF21 and Insulin Concentrations According to Administration Method The dose of the FGF21 gene was set at 500 μg, and FGF21/gCS-PEG-Lf (FGF21 gene:gCS-PEG-Lf=1:5) was administered orally to or injected intraperitoneally (i.p) into 10-week old C57BL6J mice. Three days later, the mice were sacrificed, blood was collected through the abdominal vein, and only plasma was isolated by centrifugation. ELISA experiments for FGF21 and insulin were performed on the isolated plasma.

Figure 9:
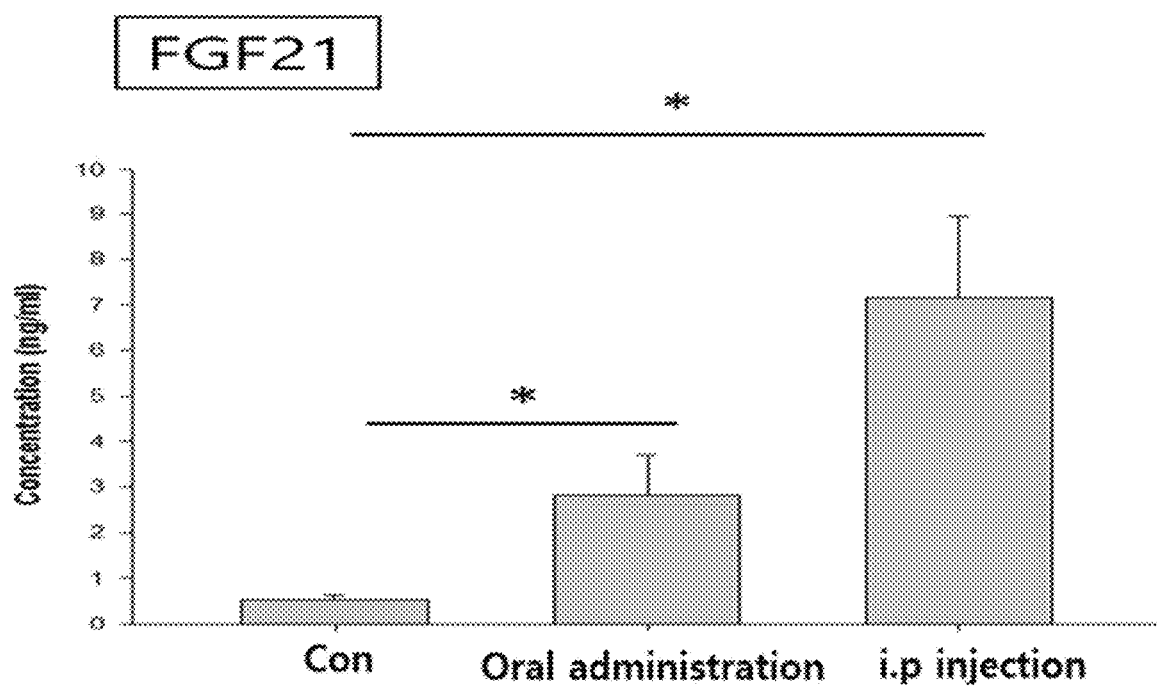
FIG. 9A illustrates the results of measuring the blood levels of an FGF21 protein after administering FGF21/gCS-PEG orally or by intraperitoneal injection to/into mice.
FIG. 9B illustrates the results of measuring blood levels of insulin after administering FGF21/gCS-PEG-Lf orally or by intraperitoneal injection to/into mice.
Figure 9B:
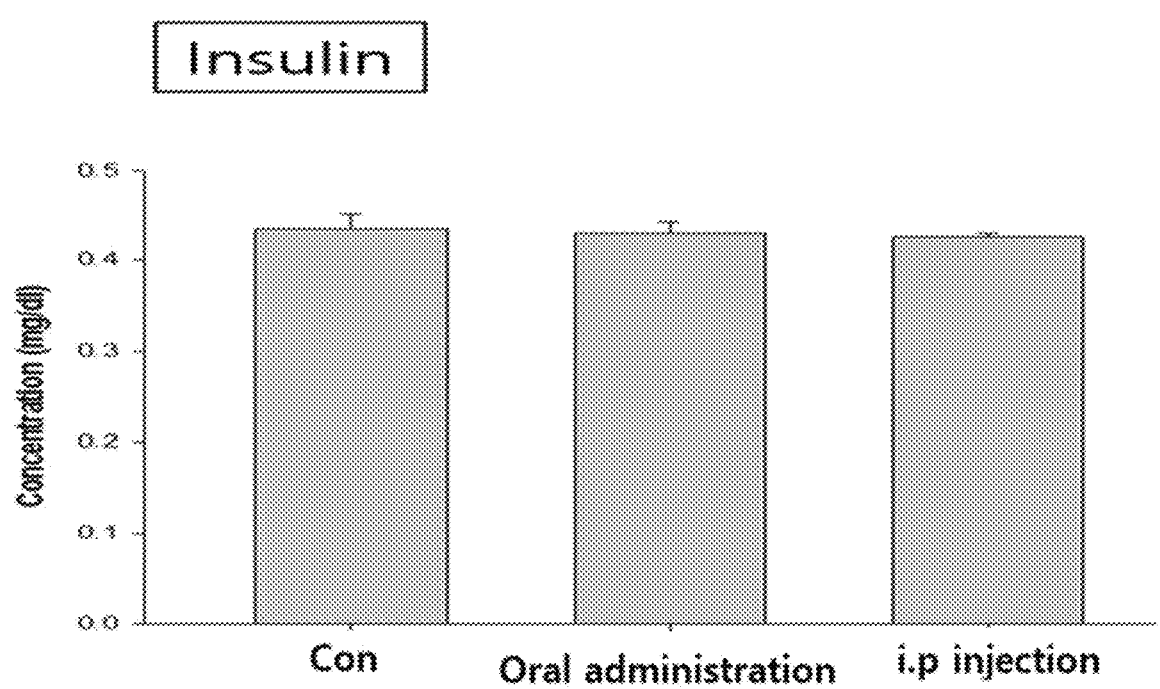

As a result, as illustrated in FIG. 9A, it could be confirmed that when FGF21/gCS-PEG-Lf was intraperitoneally injected, the blood FGF21 protein concentration was higher than when FGF21/gCS-PEG-Lf was orally administered. However, there was no significant difference in the blood insulin concentration (FIG. 9B), and since this was an experiment performed on normal mice, it was considered that there was no significant difference in the blood insulin concentration due to the fact that FGF21 affecting the amount of insulin secreted in the type 2 diabetes mellitus model did not show this effect.

Example 8: Confirmation of Endocytosis of GFP/gCS-PEG-Lf by Beta Cells of Pancreas From rats, Langerhans islets of the pancreas were separated, purified and cultured. After 5 μg of GFP and 25 μg of gCS-PEG-Lf were mixed and reacted at room temperature for 30 minutes, the Langerhans islets were treated with the reactant (GFP/gCS-PEG-Lf) for 4 hours. Four hours later, the medium was replaced, and the Langerhans islets were further cultured for 48 hours. After completion of the culture, the presence or absence of GFP expression was observed under a fluorescence microscope.

Figure 10:
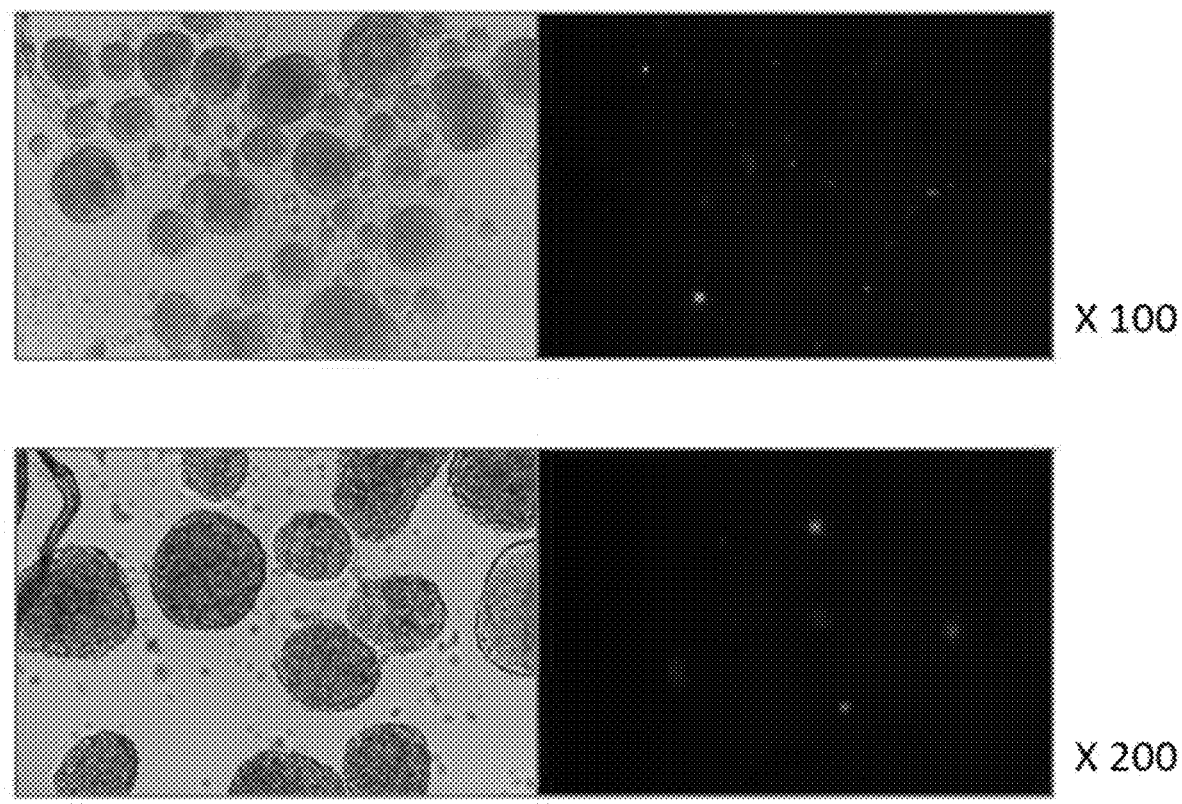
FIG. 10 illustrates the results of confirming the GFP expression levels after treating Langerhans islets of rats with GFP/gCS-PEG-Lf.

As a result, as illustrated in FIG. 10, it could be confirmed that GFP was expressed inside the Langerhans islets, which means that gCS-PEG-Lf was transferred into the Langerhans islets through endocytosis.

Example 9: Effect of Alleviating Type 2 Diabetes Mellitus by Administration of FGF21/gCS-PEG-Lf 9-1. Preparation of Type 2 Diabetes Mellitus Animal Model C57BL6J mice were classified into a normal diet group (Normal; n=5) and a high fat diet group (HFD; n=5), and fed the corresponding feed for 14 weeks. Thereafter, an insulin tolerance test (ITT) was performed in order to confirm whether type 2 diabetes mellitus was induced. After a 6-hour fast in both groups of mice, an insulin solution (0.75 U/kg) was injected intraperitoneally. After the injection, blood glucose levels were checked at a predetermined time interval.

Figure 11:
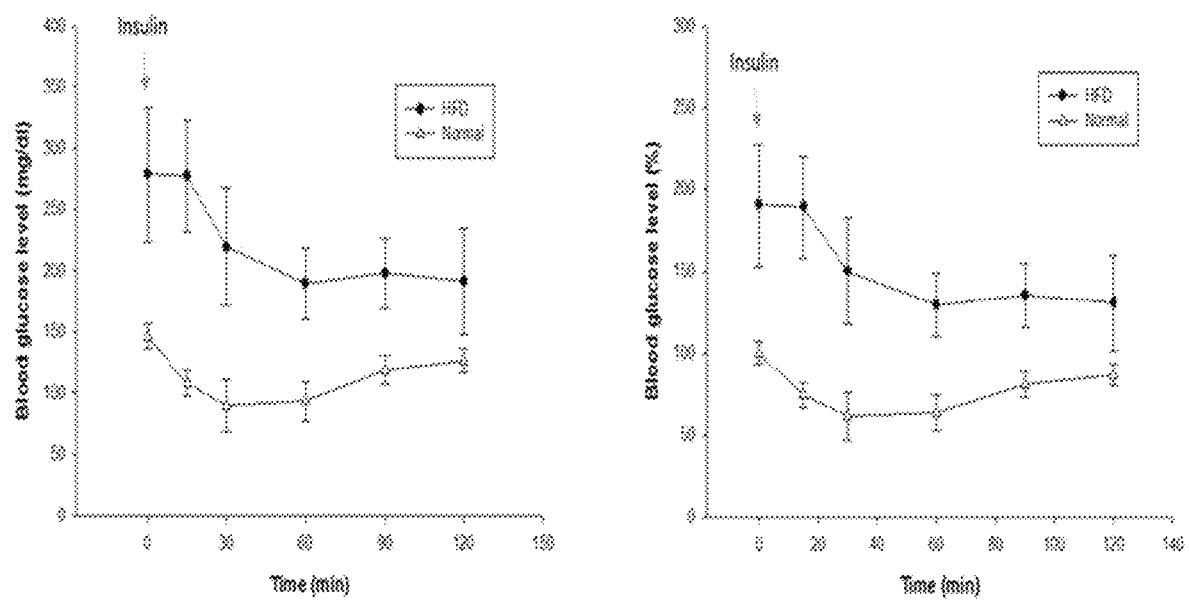
FIG. 11 illustrates the results of confirming whether type 2 diabetes mellitus is induced after supplying a high fat diet to mice by an insulin tolerance test (ITT).

As a result, as illustrated in FIG. 11, it could be confirmed that the blood glucose level was higher at all times in the high fat diet group compared to the normal diet group. From these results, it could be determined that type 2 diabetes mellitus was induced in the high fat diet group.

9-2. Effect of Improving Blood Glucose Level and Body Weight by Administration of FGF21/gCS-PEG-Lf 500 μg of the FGF21 gene was used per mouse. FGF21/gCS-PEG-Lf was obtained by reacting 500 μg of the FGF21 gene and 2500 μg of gCS-PEG-Lf at room temperature for 30 minutes. HFD mice were divided into a control (HFD control), an FGF21 short-term administration group (HFD+ FGF21 short term), and an FGF21 long-term administration group (HFD+FGF21 long term), and FGF21/gCS-PEG-Lf was orally administered once every four days. Before FGF21/gCS-PEG-Lf was orally administered, a sodium borate (SB) buffer was orally administered. FGF21/gCS-PEG-Lf was administered three times in total to the FGF21 short-term administration group, and nine times in total to the FGF21 long-term administration group. During the experiment, the body weight, food intake and non-fasting blood glucose level were measured once every two days, and the fasting blood glucose level was measured once every four days immediately before administration of FGF21/gCS-PEG-Lf.

Figure 12A:
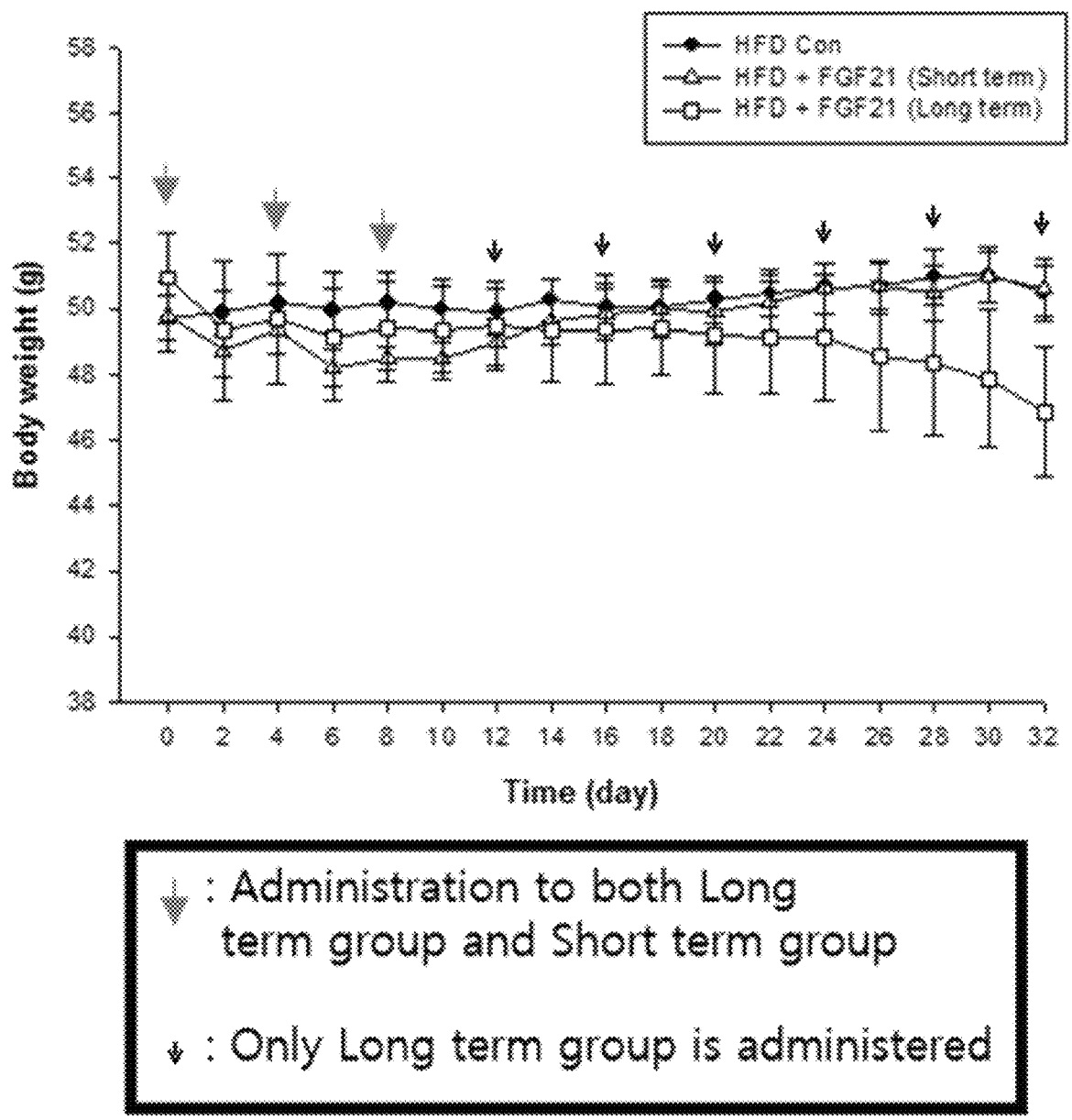
FIG. 12A illustrates the results of measuring the body weight over time while orally administering FGF21/gCS-PEG-Lf to type 2 diabetes mellitus model mice.
Figure 12B:
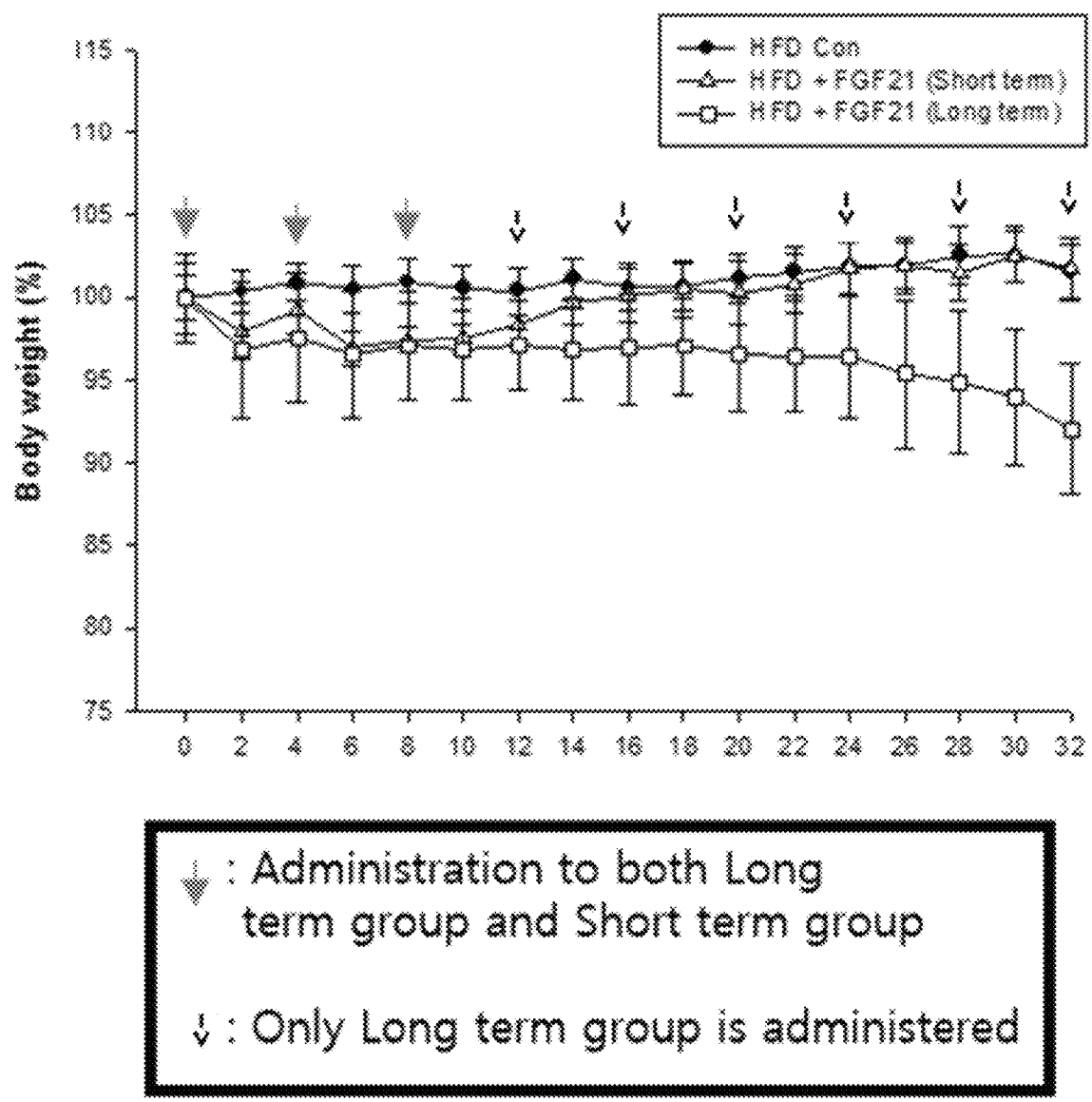
FIG. 12B illustrates the results of measuring the body weight over time while orally administering FGF21/gCS-PEG-Lf to type 2 diabetes mellitus model mice.
Figure 12C:
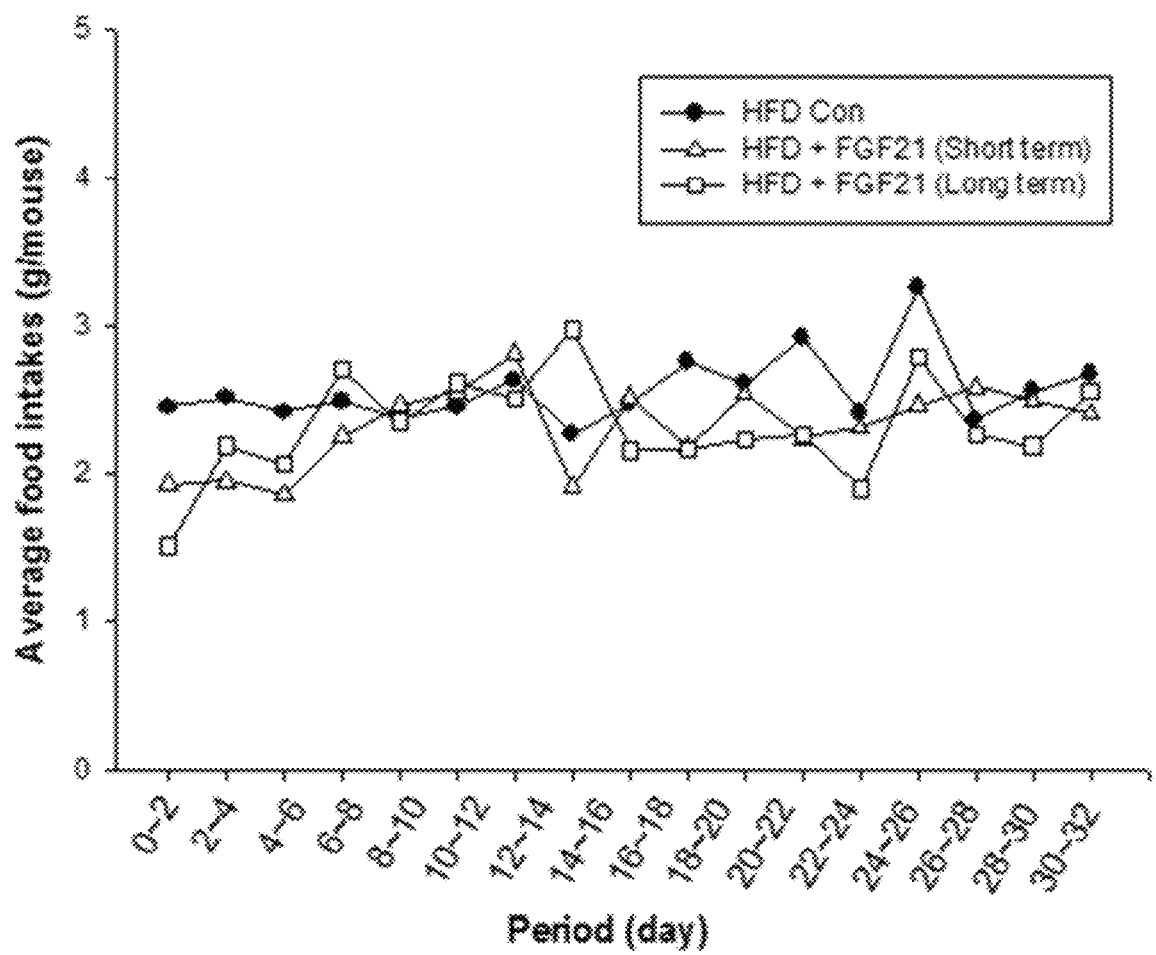
FIG. 12C illustrates the results of measuring the average feed intake over time while orally administering FGF21/gCS-PEG-Lf to type 2 diabetes mellitus model mice.
Figure 13A:
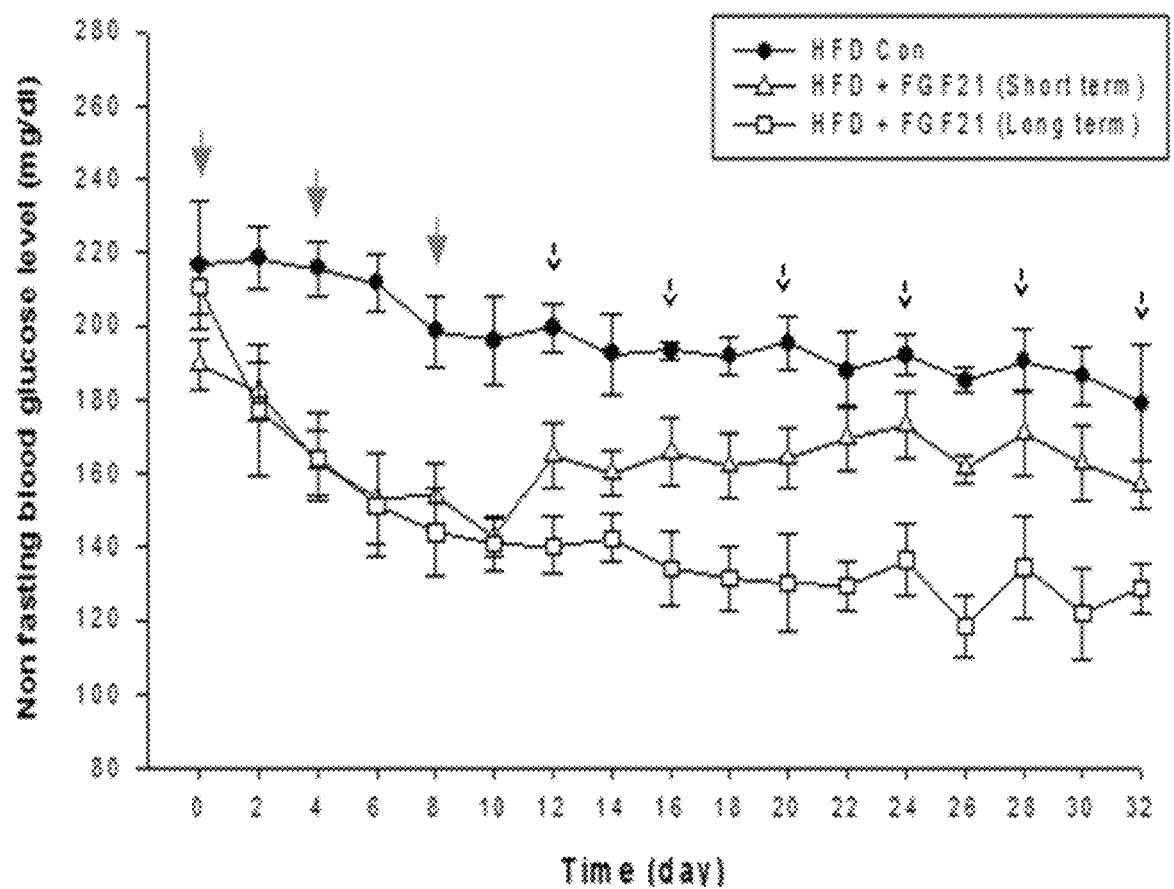
FIG. 13A illustrates the results of measuring the non-fasting blood glucose level over time while orally administering FGF21/gCS-PEG-Lf to type 2 diabetes mellitus model mice.
Figure 13B:
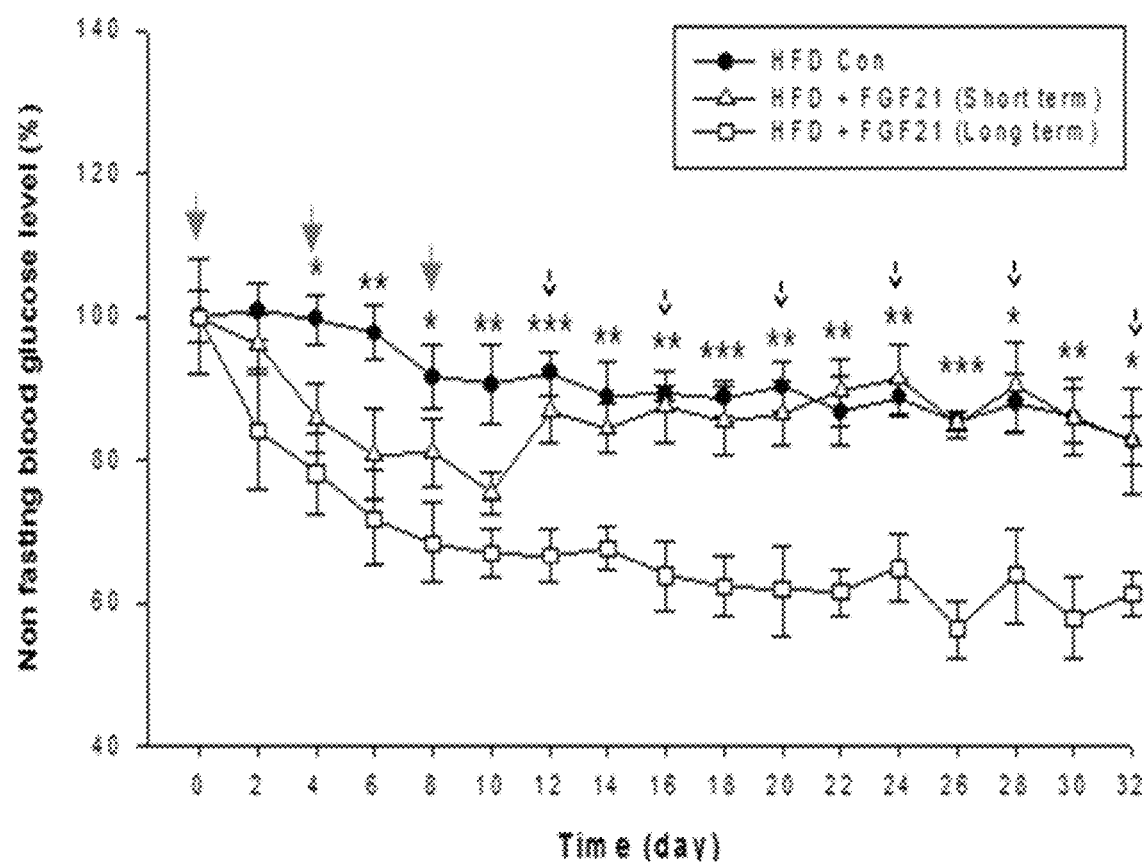
FIG. 13B illustrates the results of expressing the non-fasting blood glucose level by percentage over time while orally administering FGF21/gCS-PEG-Lf to type 2 diabetes mellitus model mice.
Figure 13C:
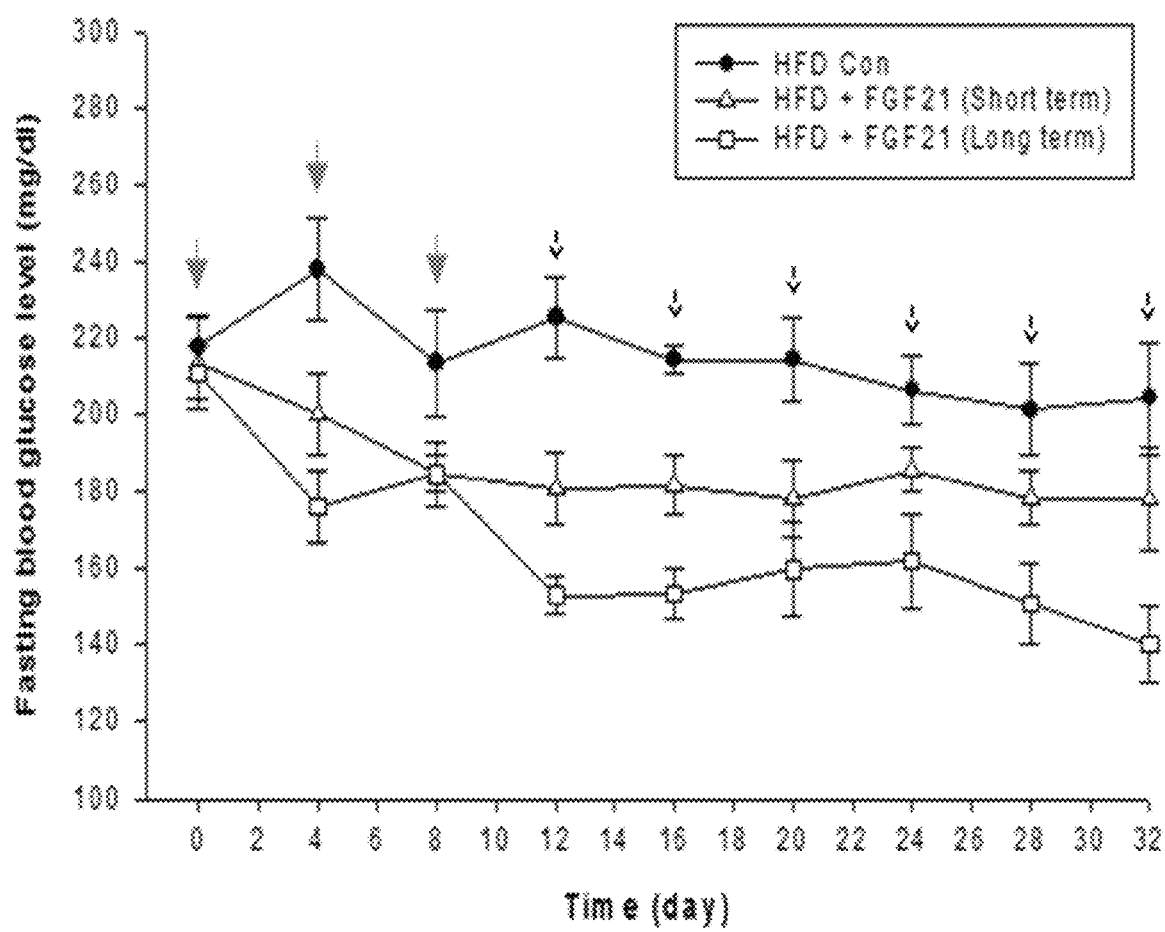
FIG. 13C illustrates the results of measuring the fasting blood glucose level over time while orally administering FGF21/gCS-PEG-Lf to type 2 diabetes mellitus model mice.
Figure 13D:
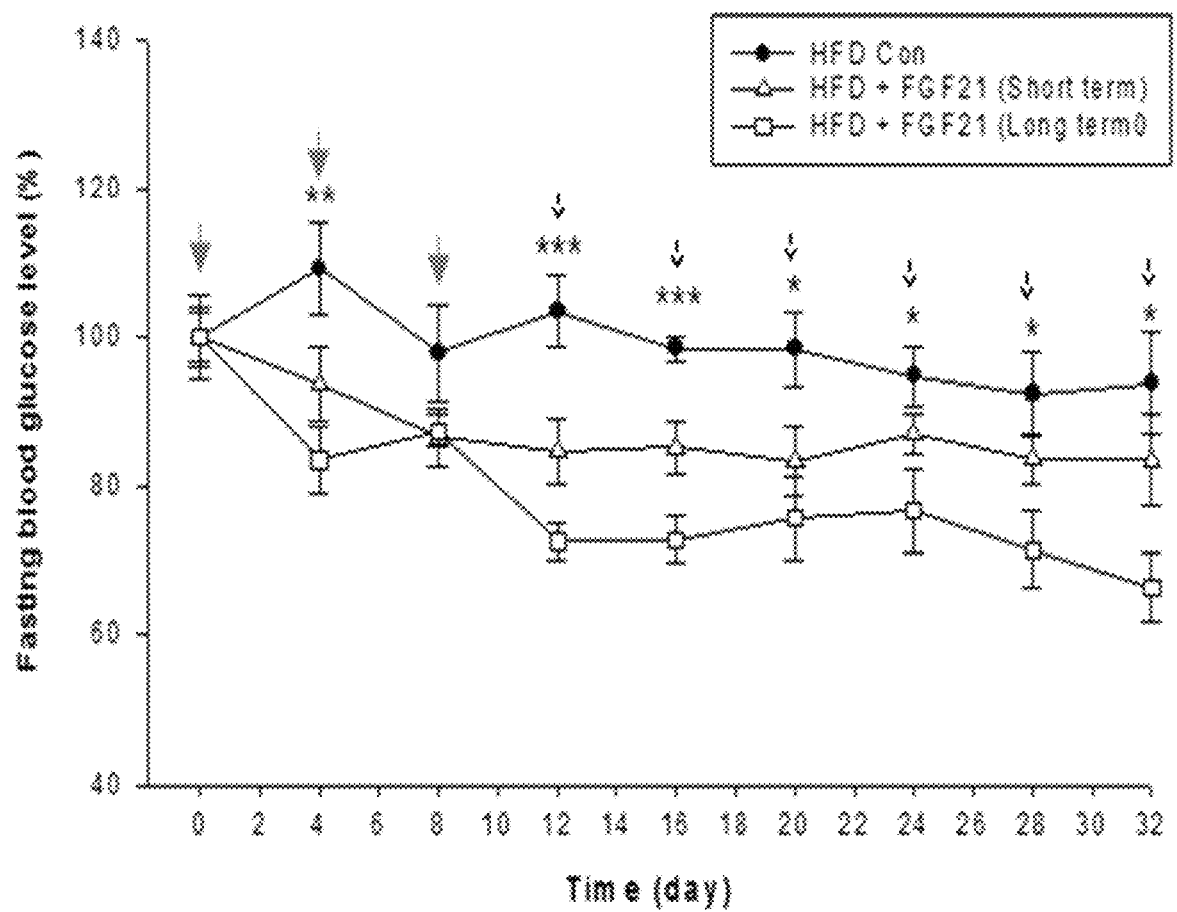
FIG. 13D illustrates the results of expressing the fasting blood glucose level by percentage over time while orally administering FGF21/gCS-PEG-Lf to type 2 diabetes mellitus model mice.

As a result, as illustrated in FIGS. 12A and 12B, it could be confirmed that as time elapsed, the body weights were decreased in the FGF21 administration groups (short term & long term). However, it could be seen that in the case of the FGF21 short-term administration group, the body weight was increased after the oral administration of FGF21/gCS-PEG-Lf was stopped. Meanwhile, there was no significant difference in food intake between the control and the FGF21 administration groups (short term & long term) (FIGS. 12C and 12D).

Furthermore, as illustrated in FIGS. 13A to 13D, the blood glucose level also exhibited a trend similar to the body weight. Through this, it could be seen that the effect of reducing body weight and blood glucose level was due to the oral administration of FGF21/gCS-PEG-Lf, and it was confirmed that the administration of FGF21/gCS-PEG-Lf was effective for the treatment of type 2 diabetes mellitus.

9-3. Confirmation of Blood FGF21 and Insulin Levels by Administration of FGF21/gCS-PEG-Lf After the completion of the oral administration experiment of FGF21/gCS-PEG-Lf, FGF21 and insulin levels were measured through ELISA (enzyme-linked immunosorbent assay, enzyme-linked immunospecific assay) by collecting blood from mice and isolating plasma.

Figure 14A:
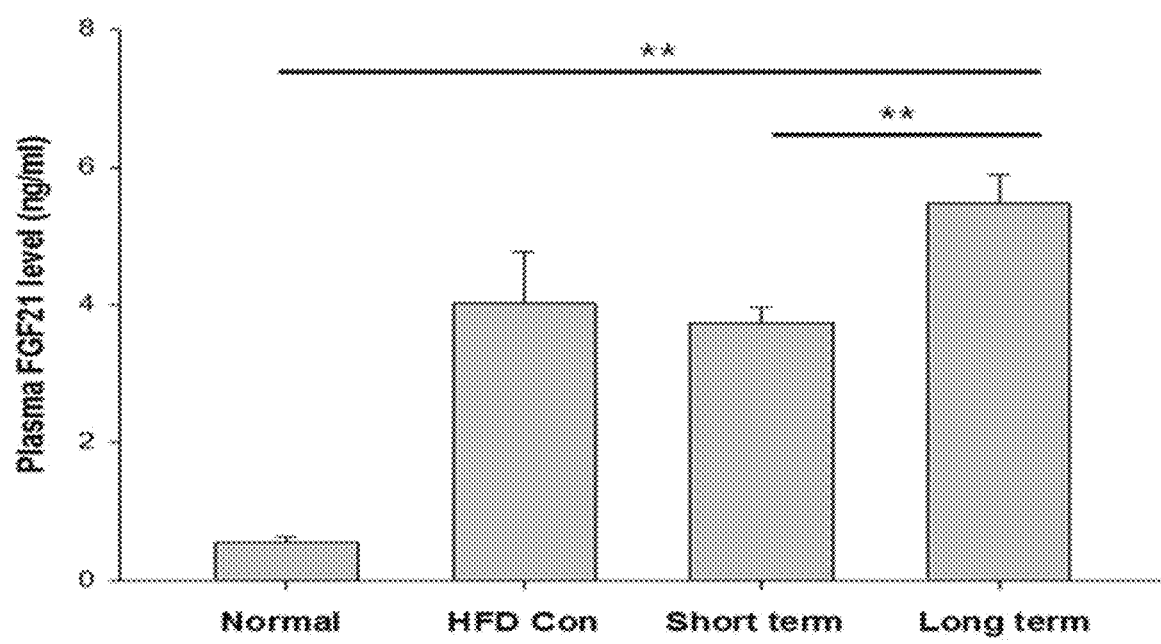
FIG. 14A illustrates the results of measuring the FGF21 levels in serum after orally administering FGF21/gCS-PEG-Lf to type 2 diabetes mellitus model mice for a short period of time or a long period of time.

As a result, as illustrated in FIG. 14A, it could be seen that in the normal group to which a HFD was not supplied, the FGF21 concentration was shown to be about 0.5 ng/ml, and the control (HFD Con) and the FGF21 short-term administration group exhibited higher FGF21 concentrations than the normal group. However, it could be confirmed that the blood FGF21 concentration in the FGF21 long-term administration group was remarkably higher than those in the other experimental groups.

Figure 14B:
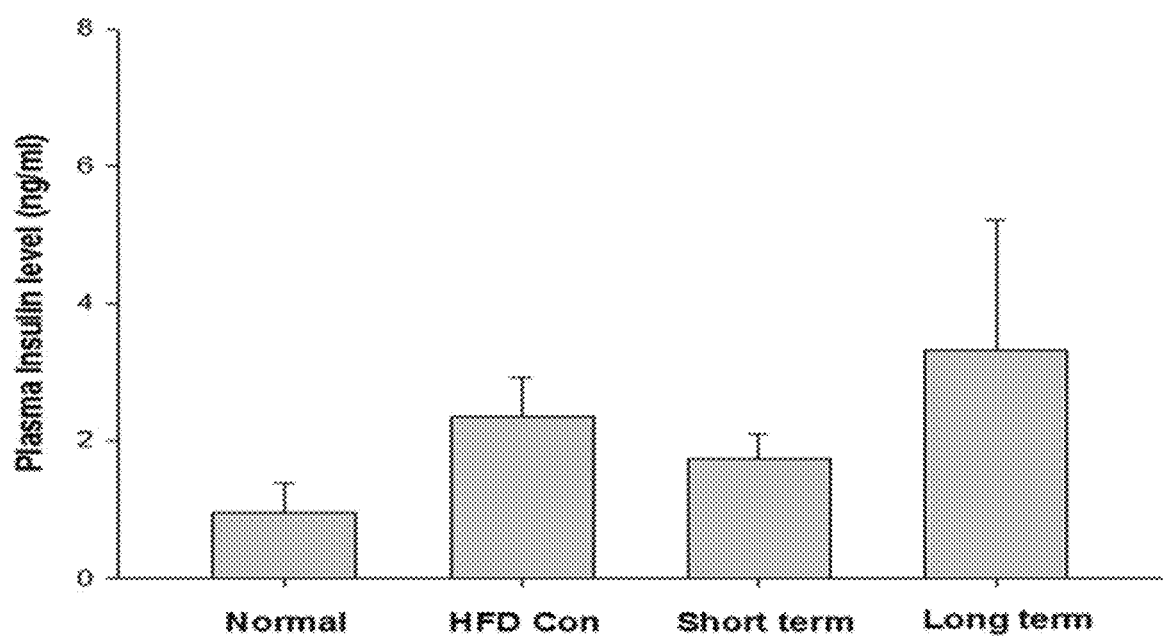
FIG. 14B illustrates the results of measuring the insulin levels in serum after orally administering FGF21/gCS-PEG-Lf to type 2 diabetes mellitus model mice for a short period of time or a long period of time.

Further, as illustrated in FIG. 14B, the blood insulin concentration also exhibited a trend similar to FGF21. The normal group exhibited the lowest concentration, and the control and the FGF21 short-term administration group showed higher concentrations. It could be seen that the insulin concentration was highest in the FGF21 long-term administration group.

It is considered that the results of the FGF21 short-term administration group and the control were similar because the FGF21 gene was removed (clearance) when a long time had elapsed after oral administration of FGF21/gCS-PEG-Lf.

Through the present experiment, it could be confirmed that the concentrations of blood FGF21 protein and insulin could be increased by orally administering FGF21/gCS-PEG-Lf.

9-4. Confirmation of Change in FGF21 and Insulin Expression Levels by Administration of FGF21/gCS-PEG-Lf After the completion of the oral administration experiment of FGF21/gCS-PEG-Lf, the brain, the duodenum, the jejunum, the ileum, the heart, the kidneys, the liver, the lungs, and the pancreas were isolated by sacrificing the mice in each experimental group. After the organs isolated according to the method in Example 5 were subjected to immunohistochemical staining, the organs were observed under a microscope.

Figure 15:
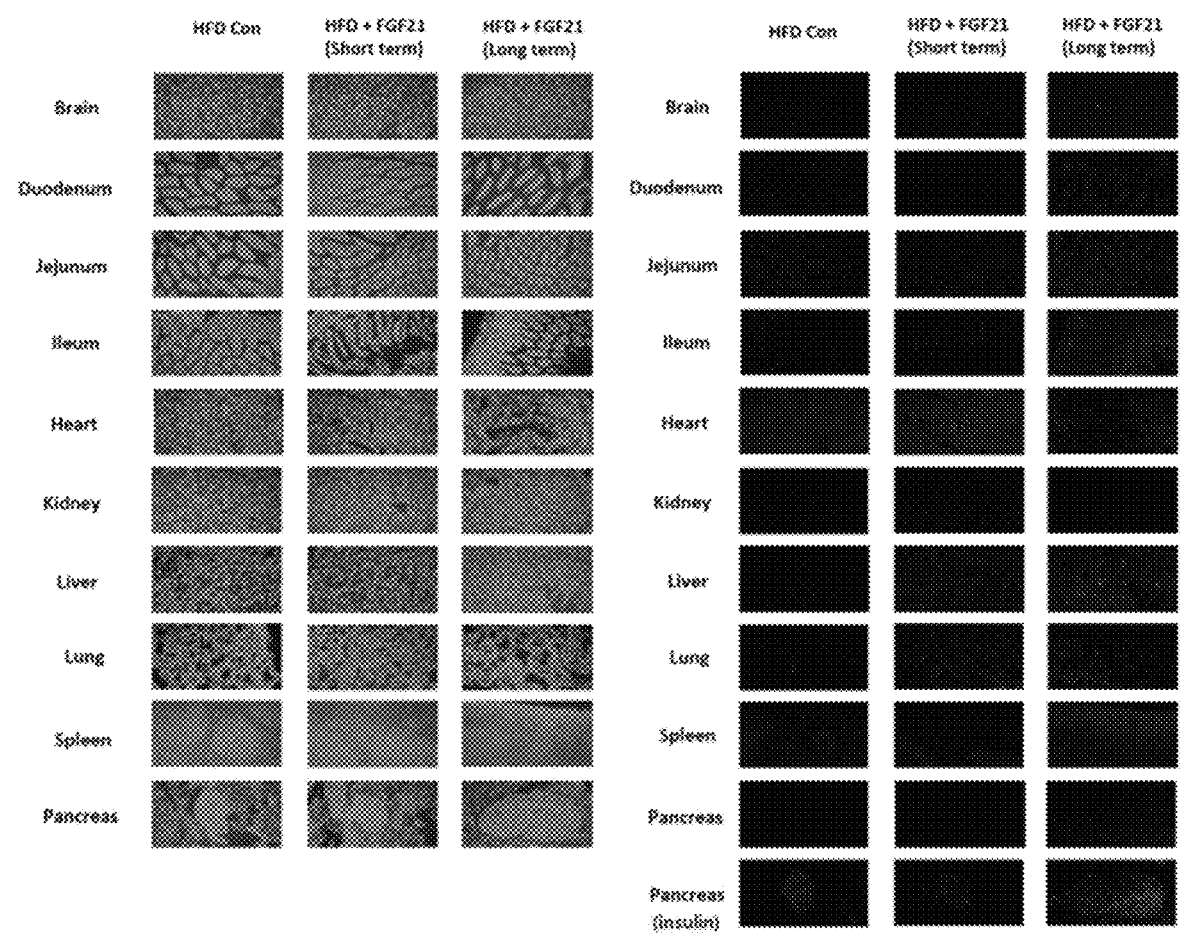
FIG. 15 illustrates the results of confirming the expression levels of FGF21 and insulin by isolating each tissue after orally administering FGF21/gCS-PEG-Lf to type 2 diabetes mellitus model mice for a short period of time or a long period of time.

As a result, as illustrated in FIG. 15, it could be seen that the expression levels of FGF21 (green) and insulin (red) in the control (HFD Con) were very low, and the FGF21 short-term administration group exhibited results similar to those of the control. However, it could be confirmed that in the FGF21 long-term administration group, the expression levels of FGF21 and insulin were high. Through these results, it was confirmed that the expression of the FGF21 protein and insulin could be induced in each organ by orally administering FGF21/gCS-PEG-Lf.

In the foregoing, the present invention has been examined mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is defined by the claims rather than the above-described description, and it should be interpreted that all the differences within a scope equivalent thereto are included in the present invention.

The invention claimed is:
1. A gene delivery complex comprising:
(a) a glycol chitosan; and
(b) pegylated lactoferrin connected to the glycol chitosan by means of a covalent bond.

2. A gene carrier comprising:
a vector comprising a target gene fragment to be delivered in vivo; and
the gene delivery complex of claim 1.

3. The gene carrier of claim 2, wherein the target gene fragment comprises the sequence of SEQ ID No. 1.

4. The gene carrier of claim 2, wherein the gene carrier has a binding ratio of the vector to the gene delivery complex of 1:2 to 1:15.

5. The gene carrier of claim 2, wherein the gene carrier is orally administered.

6. A pharmaceutical composition comprising the gene carrier of claim 2 as an active ingredient.

7. The pharmaceutical composition of claim 6, wherein the gene carrier comprises the sequence of SEQ ID No. 1.

8. The pharmaceutical composition of claim 6, wherein the pharmaceutical composition is for oral administration.

9. A method for treatment of type 2 diabetes mellitus in a subject in need thereof, the method comprising: administering orally, to the subject, an effective amount of a composition comprising the gene carrier of claim 2 as an active ingredient,
wherein the composition is for oral administration.

10. The method of claim 9, wherein the gene carrier comprises the sequence of SEQ ID No. 1.

* * * * *